US008541367B2

(12) United States Patent
Liu

(10) Patent No.: US 8,541,367 B2
(45) Date of Patent: Sep. 24, 2013

(54) PLASMA ANTI-DIABETIC NUCB2 PEPTIDE (PLADIN) AND USES THEREOF

(75) Inventor: Jian-ning Liu, Brighton, MA (US)

(73) Assignee: Landing Biotech, Inc., Newton, MA (US)

( * ) Notice: Subject to any disclaimer, the term of this patent is extended or adjusted under 35 U.S.C. 154(b) by 557 days.

(21) Appl. No.: 12/722,575

(22) Filed: Mar. 12, 2010

(65) Prior Publication Data
US 2010/0235935 A1 Sep. 16, 2010

Related U.S. Application Data

(60) Provisional application No. 61/253,603, filed on Oct. 21, 2009, provisional application No. 61/159,574, filed on Mar. 12, 2009.

(51) Int. Cl.
A61K 38/00 (2006.01)

(52) U.S. Cl.
USPC ............... 514/6.8; 514/1.1; 514/6.7; 514/6.9; 530/300

(58) Field of Classification Search
None
See application file for complete search history.

(56) References Cited

U.S. PATENT DOCUMENTS

| 7,795,390 | B2* | 9/2010 | Mori et al. | 530/350 |
|---|---|---|---|---|
| 2004/0220140 | A1 | 11/2004 | Vournakis et al. | |
| 2005/0196421 | A1 | 9/2005 | Hunter et al. | |
| 2008/0115231 | A1 | 5/2008 | Mori et al. | |
| 2010/0234274 | A1* | 9/2010 | Liu | 514/4 |
| 2011/0142937 | A1 | 6/2011 | MacDonald | |

FOREIGN PATENT DOCUMENTS

| CN | 101914150 A | 12/2010 |
|---|---|---|
| EP | 1132083 A2 | 9/2001 |
| EP | 1900813 A1 | 3/2008 |
| EP | 1986008 A1 | 10/2008 |
| EP | 2229952 | 9/2010 |

OTHER PUBLICATIONS

European Extended Search Report, Jul. 16, 2010, Jian-ning Liu, European App'l No. 10156306.2, filed, Mar. 12, 2010.
U.S. Office Action, Jun. 24, 2011, Jian-ning Liu, U.S Appl. No. 12/402,848, filed Mar. 12, 2009.
Chua et al., 1996, "Phenotypes of Mouse Diabetes and Rat Fatty Due to Mutations in the OB (Leptin) Receptor", Science, vol. 271 (5251): 994-996.
Cota et al., 2006, "Hypothalamic mTOR signaling Regulates Food Intake", Science, vol. 312, (5775): 927-930.
Cushman et al., 1999, "Fibrinolytic Activation Markers Predict Myocardial Infraction in the Elderly", Arteriosclerosis Thrombosis and Vascular Biology, vol. 19:493-498.
Ding et al., 2003, "Lung Endothelium Targeting for Pulmonary Embolism Thromnolysis", Circulation, vol. 108: 2892-2898.
Enriori et al., 2007, "Diet-Induced Obesity Causes Severe but Reversible Leptin Resistance in Arcuate Melanocortin Neurons", Cell Metabolism, vol. 5, 181-194.
Folsom et al., 2001, "Prospective Study of Fibrinolytic Factors and Incident Coronary Heart Disease: The Atherosclerosis Risk in Communities (ARIC) Study", Arteriosclerosis Thrombosis and Vascular Biology, vol. 21: 611-617.
Furth et al., 1970, "Studies on the Chemical Modification of the Tyrosine Residue in Bovine Neurophysin-II", Biochemical Journal, vol. 116: 545-553.
Gonzalez et al., 2009, "Pancreatic Beta Cells Colocalize Insulin and Pronesfatin Immunoreactivity in Rodents", Biochemical and Biophysical Research Communications, vol. 381:643-648.
Hastings et al., 1997, "Neurospin, a Brain-associated Inhibitor of Tissue Plasminogen Activator is Localized Primarily in Neurons", The Journal of Biological Chemistry, vol. 272(5):33062-33067
Hoover-Plow et al., 1999, "Growth and Behavioral Development in Plasminogen Gene-Targeted Mice", Growth, Development, and Aging, vol. 63 (1-2): 13-32.
Krystosek et al., 1981, "Plasminogen Activator Release at the Neuronal Growth Cone", Science, vol. 213 (4515): 1532-1534.
Merali et al., 2008, "Nesfatin-1 Increases Anxiety-and Fear-related Behaviors in the Rat", Psychopharmacology, vol. 201:115-123.
Miller et al., 2002, "Gene Expression Patterns in Calorically Restricted Mice: Partial Overlap with Lon-Lived Mutant Mice", Molecular Endocrinology, vol. 16(11): 2657-2666.
Moller et al., 2001, "New Drug Targets for Type 2 Diabetes and the Metabolic Syndrome", Nature, vol. 414: 821-827.
Moonen et al., 1982, "Plaminogen Activator-Plasmin System and Neuronal Migration", Nature, vol. 298: 753-755.
Oh-I et al., 2006, "Identification of Nesfatin-1 as a Satiety Molecule in the Hypothalamus", Nature, vol. 443 (7112): 709-712.
Pan et al., 2007, "Nesfatin-1 Crosses the Blood-Brain Barrier without Saturation", Peptides, vol. 28: 2223-2228.
Pang et al., 2004, "Cleavage of proBDNF by tPA/Plasmin is Essential for Long-Term Hippocampal Plasticity", Science, vol. 306(5695): 487-491.
Price et al., 2007, "Permeability of the Blood-Brain Barrier to a Novel Satiety Molecule of Nesfatin-1", Peptides, vol. 28: 2372-2381.
Sakkinen et al., 1999, "Relationship of Plasmin Generation to Cardiovascular Disease Risk Factors in Elderly Men and Women", Arteriosclerosis Thrombosis and Vascular Biology, vol. 19: 499-504.
Schafer et al., 2001, "Disruption of the Plasminogen Activator Inhibitor 1 Gene Reduces the Adiposity and Improves the Metabolic Profile of Genetically Obese and Diabetic ob/ob Mice", The FASEB Journal, vol. 15 (10):1840-1842.
Selvarajan et al., 2001, "A Plasma Kallikrein-Dependent Plasminogen Cascade Required for Adipocyte Differentiation", Nature Cell Biology, vol. 3: 267-275.

(Continued)

Primary Examiner — Janice Li
(74) Attorney, Agent, or Firm — Law Offices of Albert Wai-Kit Chan, PLLC

(57) ABSTRACT

The present invention provides pladin (plasma anti-diabetic nucb2 peptide) polypeptide and functional equivalent thereof that are useful for treating diabetes. The present invention provides a method of treating diabetes by administering to a subject nesfatin-1, pladin, or a functional equivalent thereof. The present invention also provides a method of treating diabetes by administering to subject plasmin inhibitors.

9 Claims, 19 Drawing Sheets

(56) References Cited

OTHER PUBLICATIONS

Shimizu et al., 2009, "Peripheral Administration of Nesftin-1 reduces Food Intake in Mice: the Leptin-Independent Mechanism", Endocrinology, vol. 150: 662-671.

Stengel et al., 2009, "Identification and Characterization of Nestafin-1 Immunoreactivity in Endocrine Cell Types of the Rat Gastric Oxyntic Mucosa", Endocrinology, vol. 150(1): 232-238.

Tsirka et al., 1997, "An Extracellular Proteolytic Cascade Promotes Neuronal Degeneration in the Mouse Hippocampus", The Journal of Neuroscience, vol. 17(2): 543-552.

Wang et al., 2004, "Plasminogen Regulates Pro-Opiomelanocortin Processing", Journal of Thrombosis and Haemostasis, vol. 2:785-796.

Zhang et al., 2002, "Endogenous Plasmin Converts Glu-Plasminogen to Lys-Plasminogen on the Monocytoid Cell Surface", Journal of Thrombosis and Haemostasis. vol. 1: 1254-1270.

Zheng et al., 2004, Development of Alburninuria and Glomerular Lesions in Normaglycernic B6 Recipients of db/db Mice Bone Marrow, Diabetes, vol. 53: 2420-2427.

Zuccollo et al., 1997, "Effects of Aprotinin on the Kallilrein-Kinin System in Type I Diabetes (Insulitis)", Immunopharmacology, vol. 37(2-3):251-256.

Chinese Office Action, Nov. 24, 2011 for Chinese Application No. 201010147877.5, filed Mar. 22, 2010.

U.S. Final Office Action, Nov. 29, 2011 for U.S. Appl. No. 12/402,848, filed Mar. 12, 2009.

U.S. Office Action, Apr. 12, 2012 for U.S. Appl. No. 12/402,848, filed Mar. 12, 2009.

\* cited by examiner

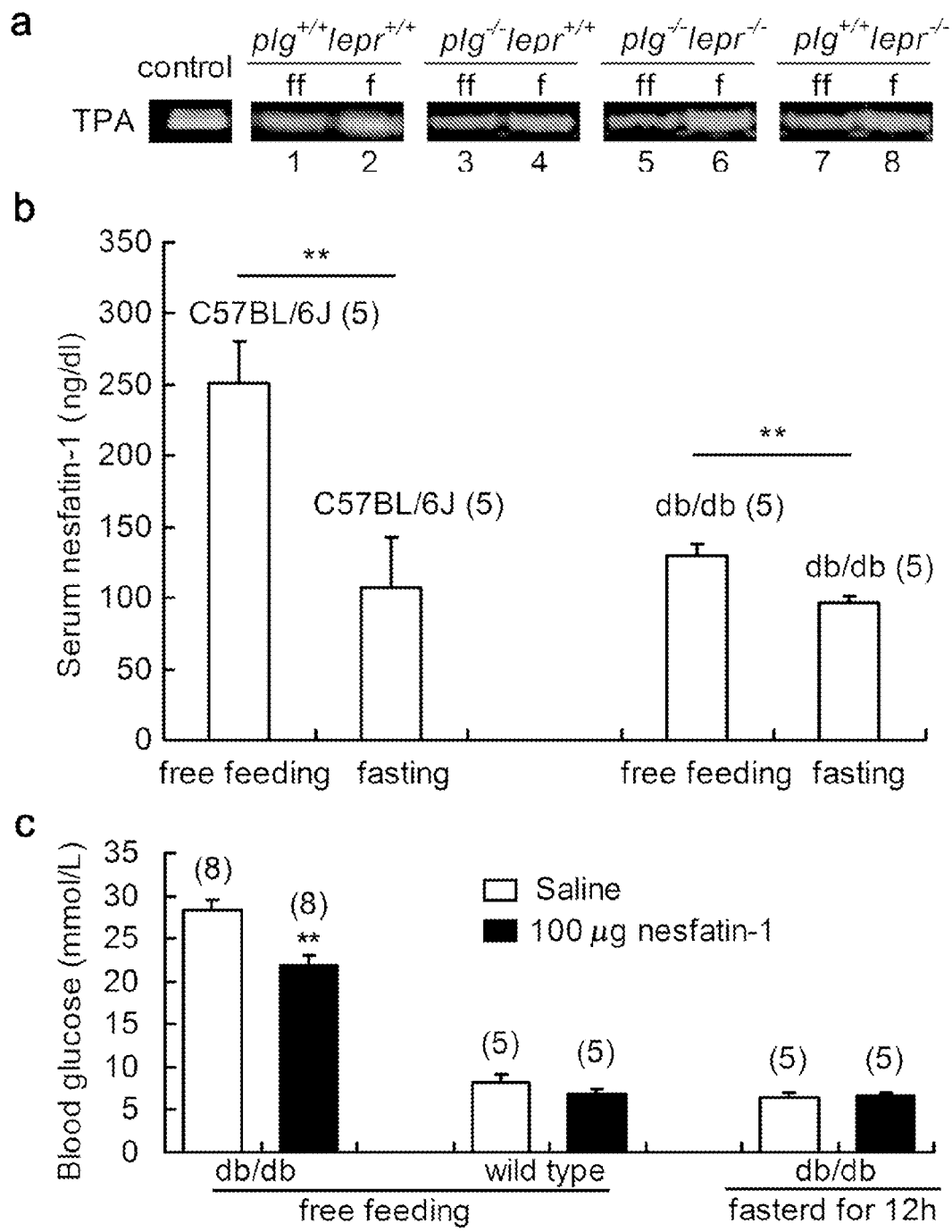
Figure 4a-c

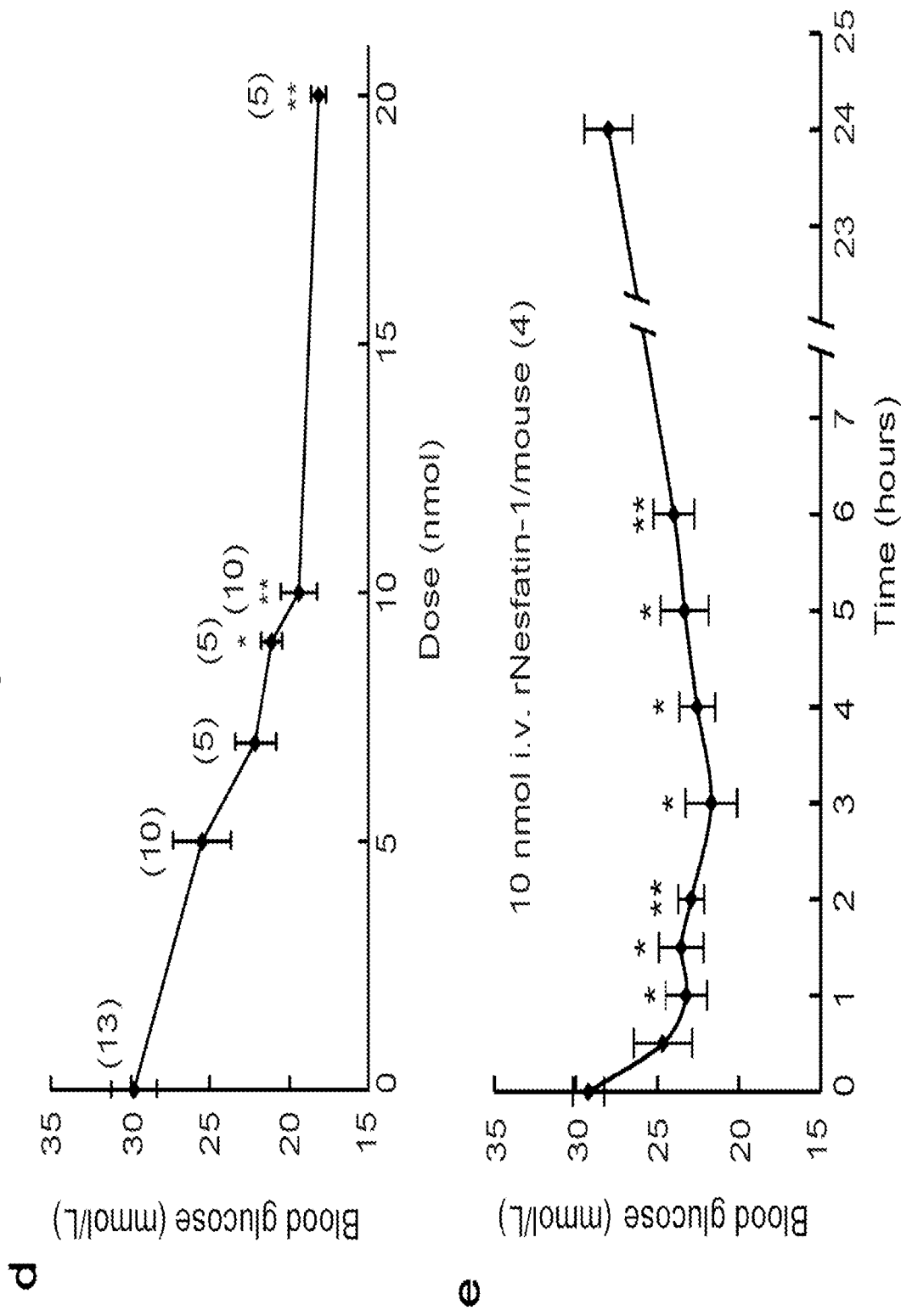
Figure 4d-e

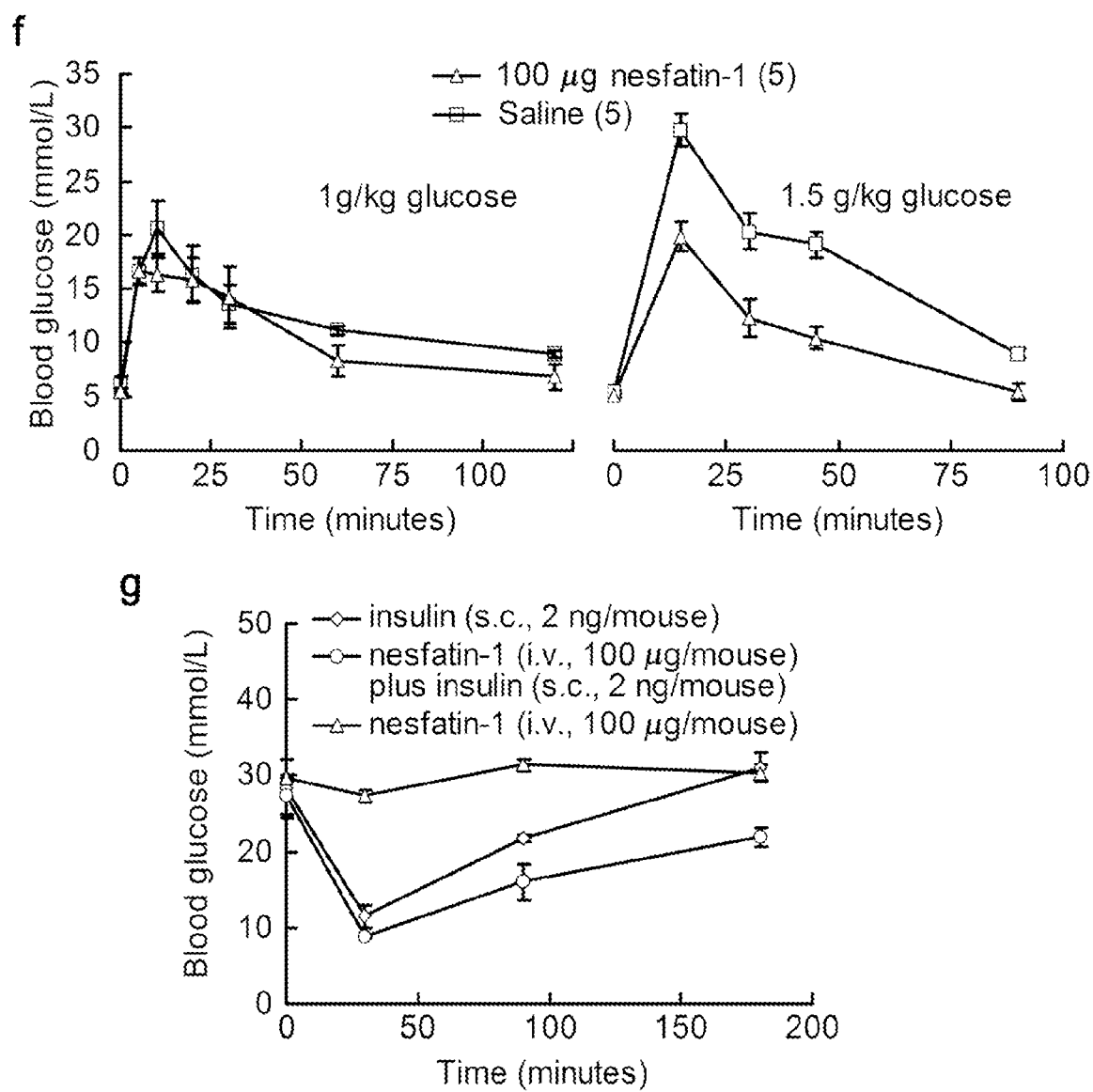
Figure 4f-g

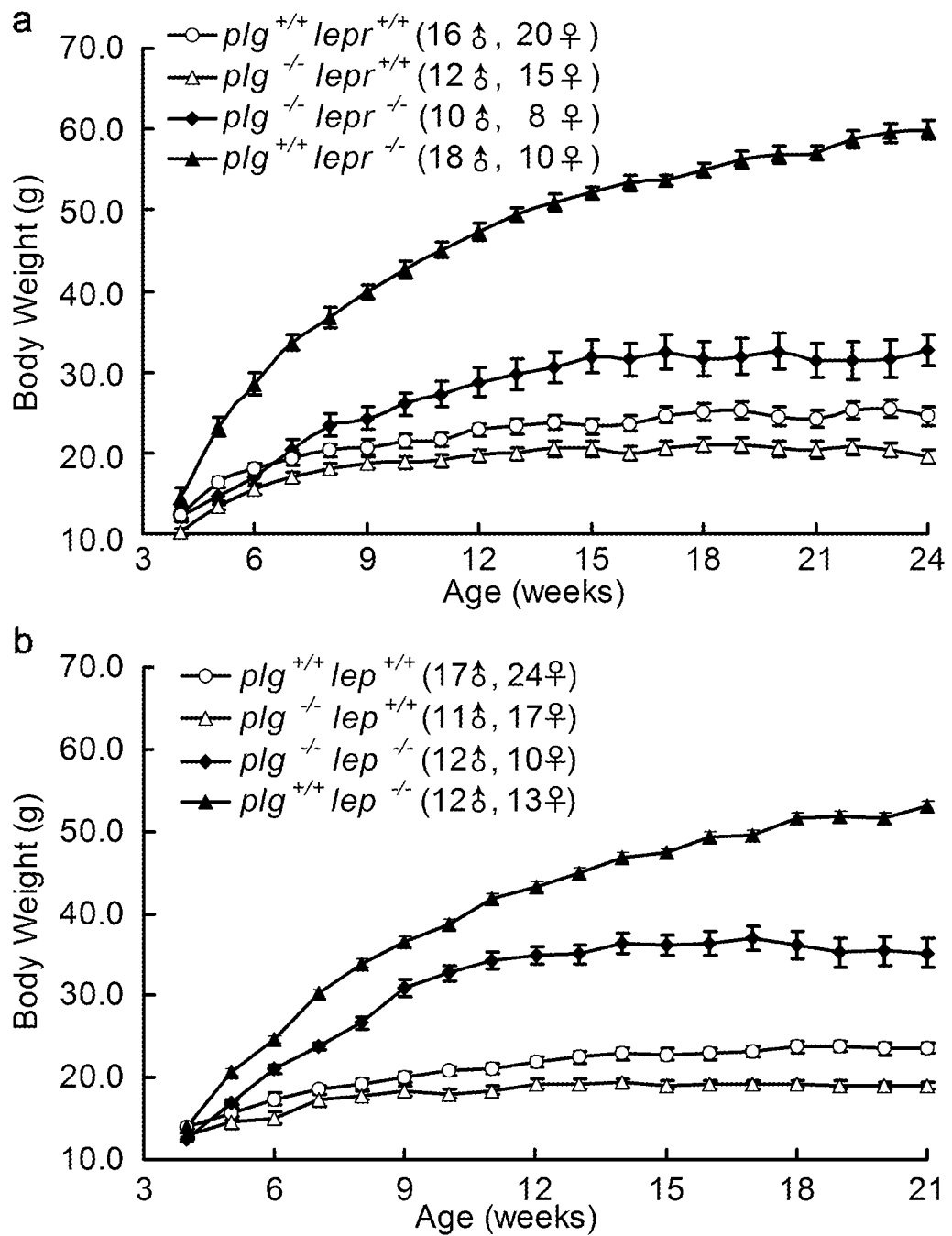
Figure 7a-b

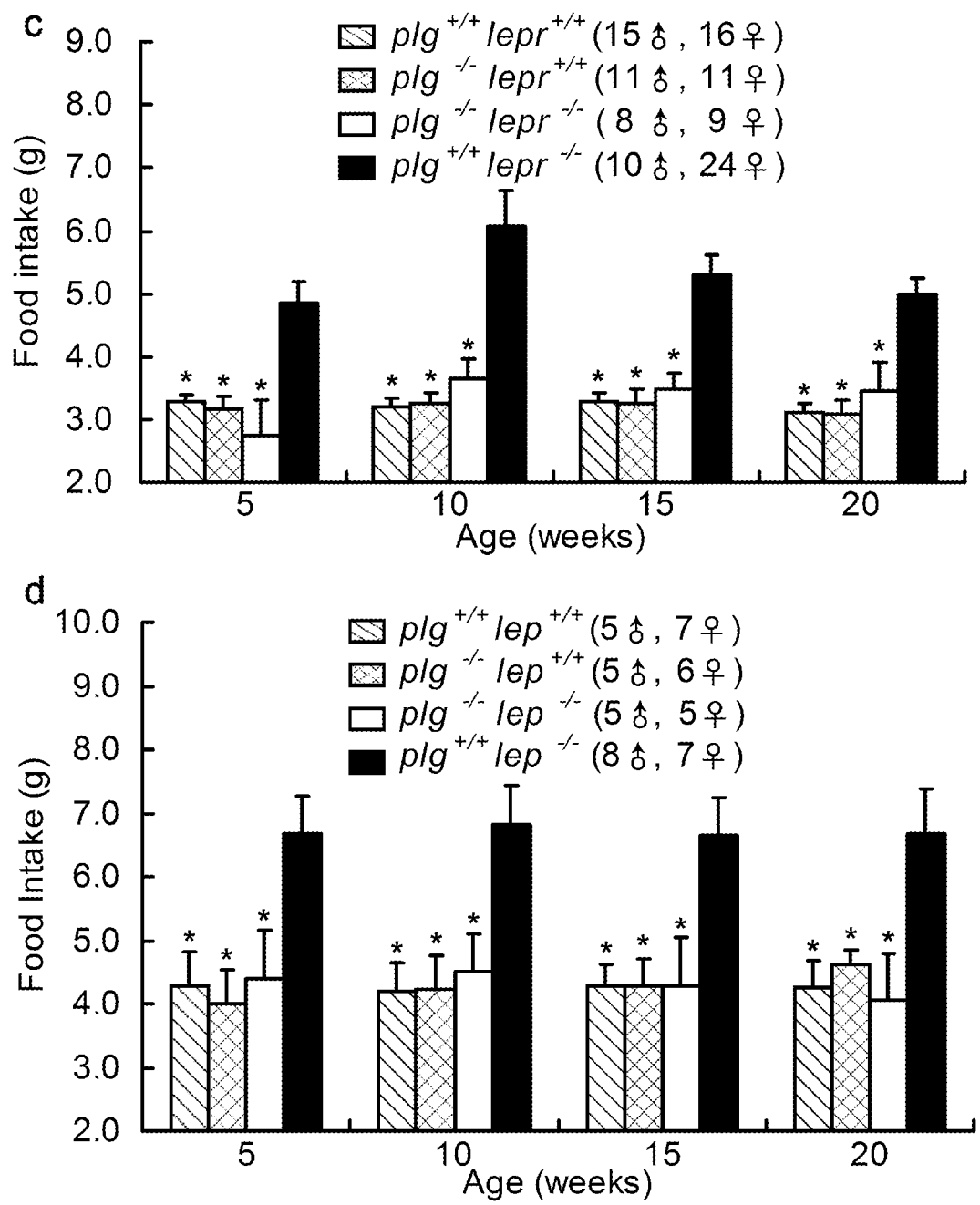
Figure 7c-d

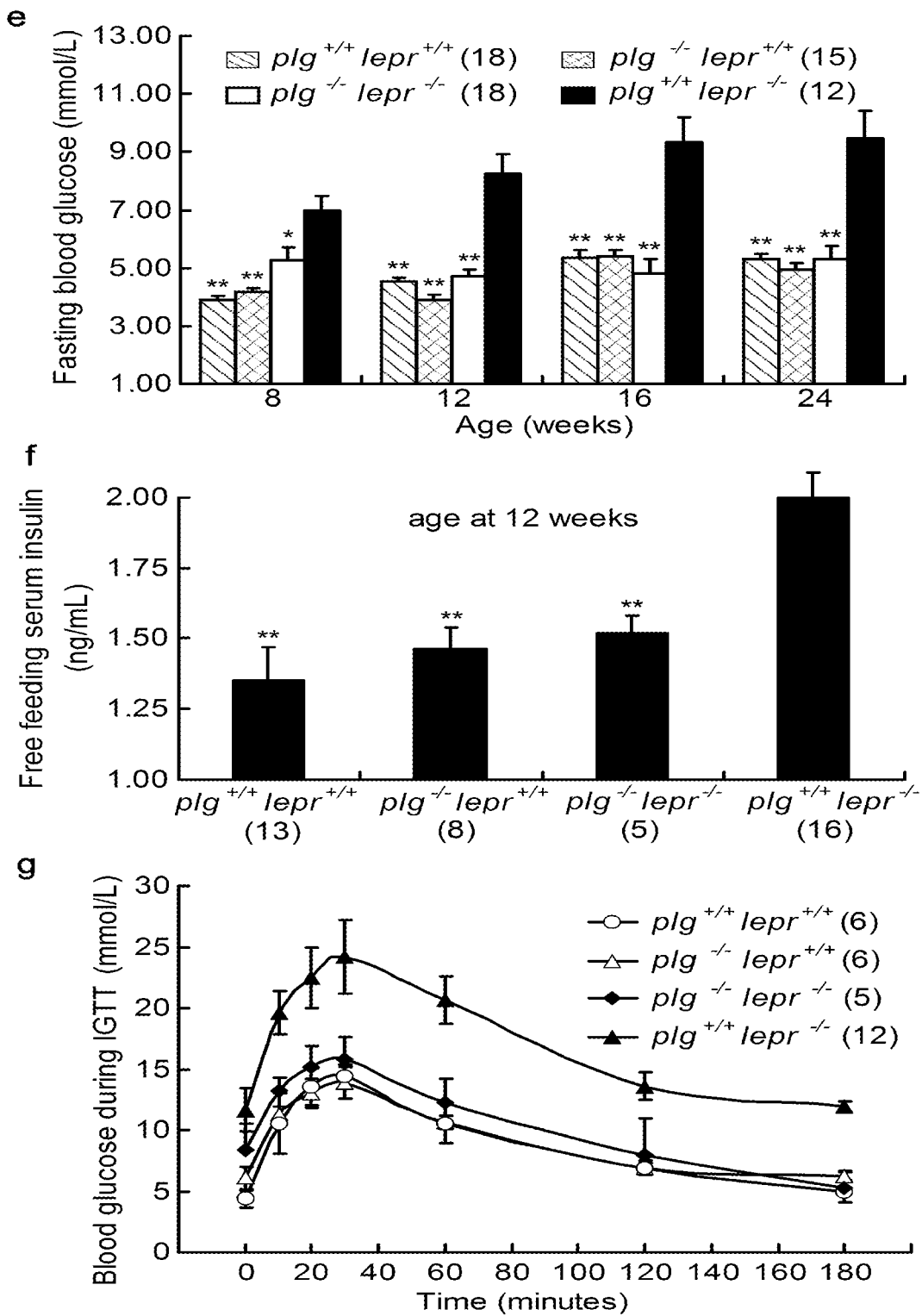
Figure 7e-g

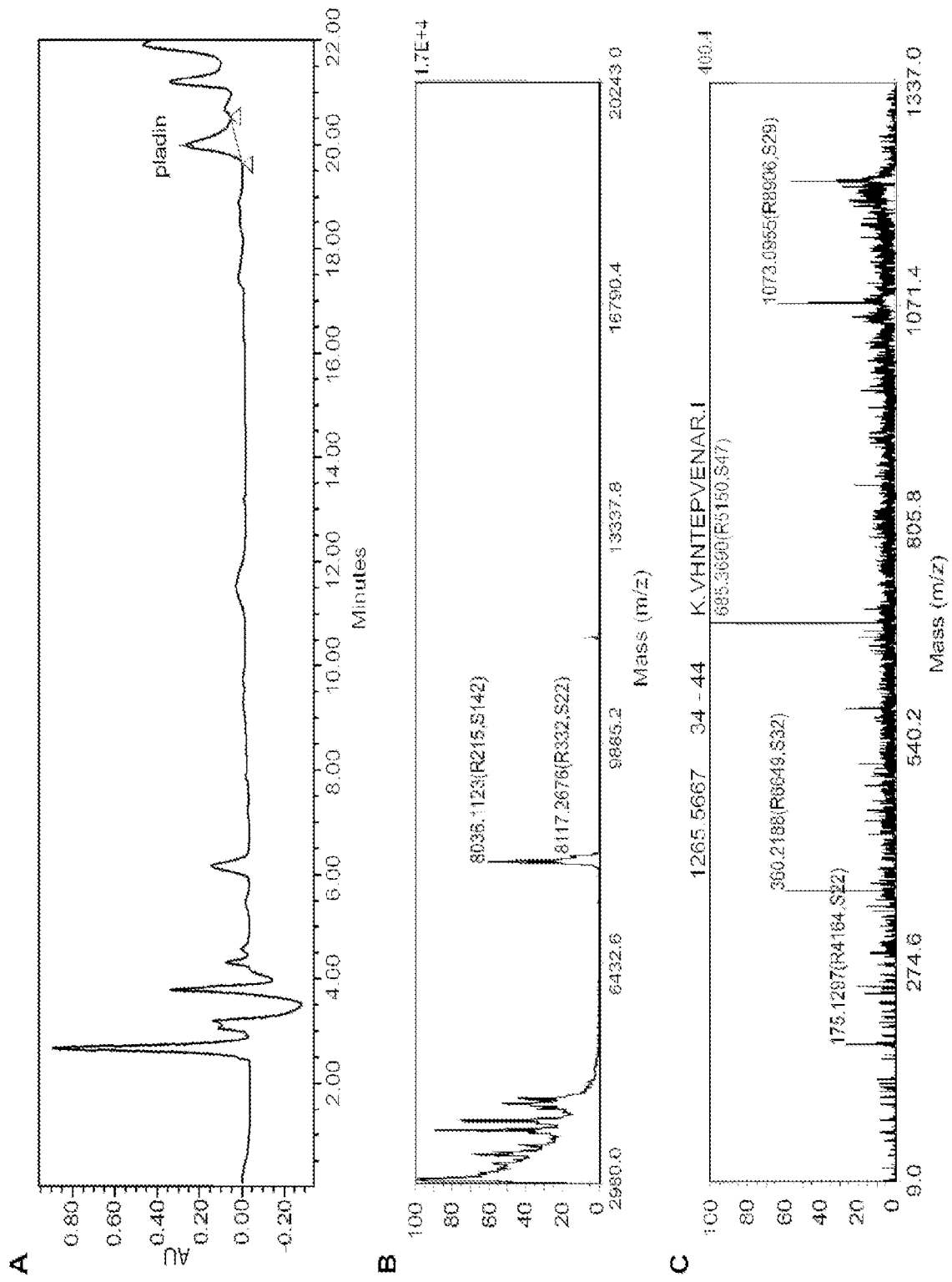
Figure 9a-c

Figure 9d-e
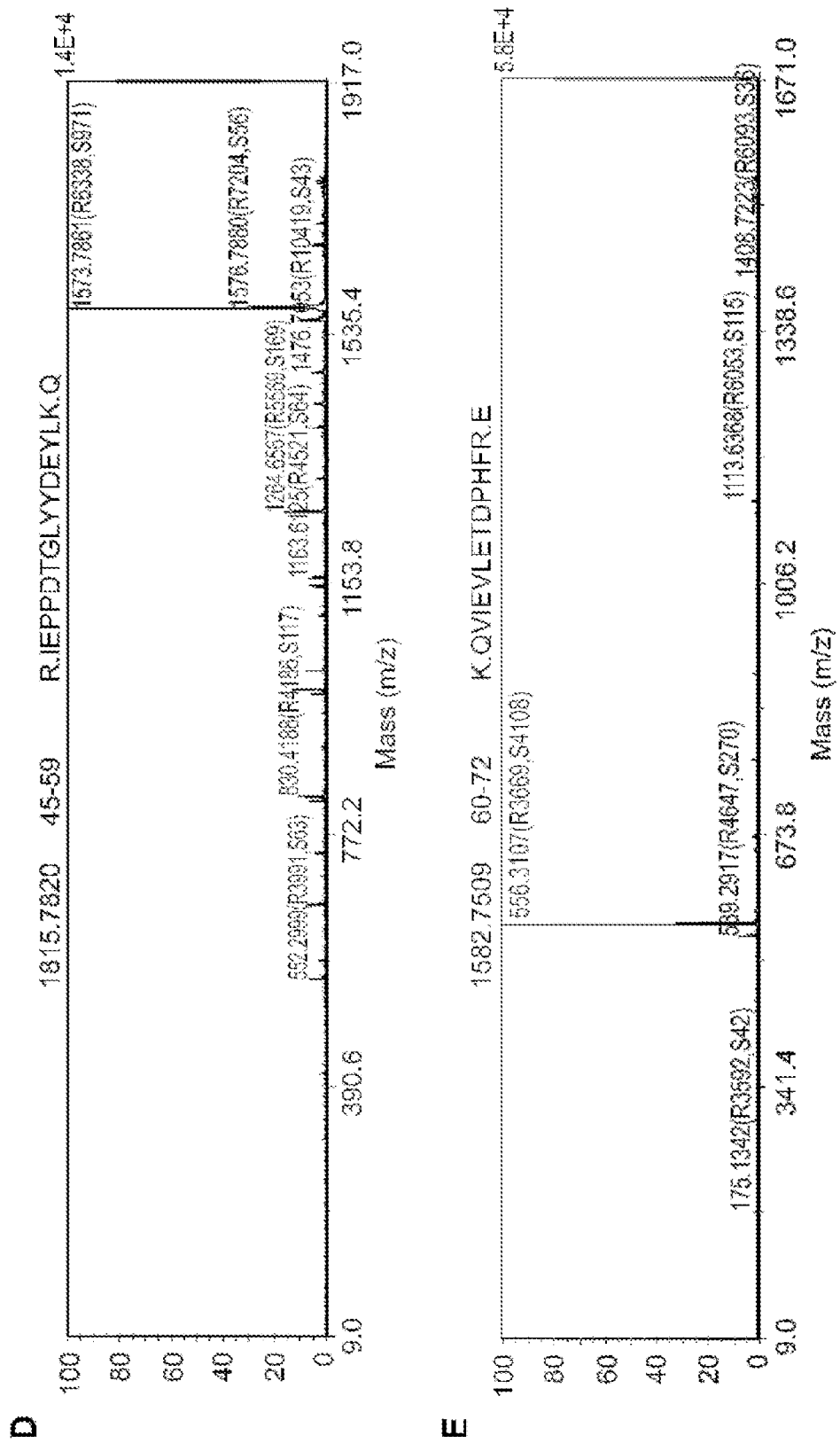

SEQUENCE LISTING

<160> NUMBER OF SEQ ID NOS: 25

<210> SEQ ID NO 1
<211> LENGTH: 17
<212> TYPE: DNA
<213> ORGANISM: Artificial Sequence
<220> FEATURE:
<223> OTHER INFORMATION: Primer for genotyping by PCR

<400> SEQUENCE: 1
tacattttga tggaggg                                                  17

<210> SEQ ID NO 2
<211> LENGTH: 17
<212> TYPE: DNA
<213> ORGANISM: Artificial Sequence
<220> FEATURE:
<223> OTHER INFORMATION: Primer for genotyping by PCR

<400> SEQUENCE: 2
tacattttga tggaggt                                                  17

<210> SEQ ID NO 3

```
<211> LENGTH: 17
<212> TYPE: DNA
<213> ORGANISM: Artificial Sequence
<220> FEATURE:
<223> OTHER INFORMATION: Primer for genotyping by PCR

<400> SEQUENCE: 3
ggaatctaat atggaag                                                    17

<210> SEQ ID NO 4
<211> LENGTH: 17
<212> TYPE: DNA
<213> ORGANISM: Artificial Sequence
<220> FEATURE:
<223> OTHER INFORMATION: Primer for genotyping by PCR

<400> SEQUENCE: 4
tgacctggag aatctcc                                                    17

<210> SEQ ID NO 5
<211> LENGTH: 17
<212> TYPE: DNA
<213> ORGANISM: Artificial Sequence
<220> FEATURE:
<223> OTHER INFORMATION: Primer for genotyping by PCR

<400> SEQUENCE: 5
tgacctggag aatctct                                                    17

<210> SEQ ID NO 6
<211> LENGTH: 17
<212> TYPE: DNA
<213> ORGANISM: Artificial Sequence
<220> FEATURE:
<223> OTHER INFORMATION: Primer for genotyping by PCR

<400> SEQUENCE: 6
catccaggct ctctggc                                                    17

<210> SEQ ID NO 7
<211> LENGTH: 24
<212> TYPE: DNA
<213> ORGANISM: Artificial Sequence
<220> FEATURE:
<223> OTHER INFORMATION: Primer for genotyping by PCR

<400> SEQUENCE: 7
tgtgggctct aaagatggaa ctcc                                            24

<210> SEQ ID NO 8
<211> LENGTH: 29
<212> TYPE: DNA
<213> ORGANISM: Artificial Sequence
<220> FEATURE:
<223> OTHER INFORMATION: Primer for genotyping by PCR

<400> SEQUENCE: 8
gtgcgaggcc agaggccact tgtgtagcg                                       29

<210> SEQ ID NO 9
<211> LENGTH: 24
<212> TYPE: DNA
<213> ORGANISM: Artificial Sequence
<220> FEATURE:
<223> OTHER INFORMATION: Primer for genotyping by PCR

<400> SEQUENCE: 9
```

```
tgtgggctct aaagatggaa ctcc                                          24
```

<210> SEQ ID NO 10
<211> LENGTH: 20
<212> TYPE: DNA
<213> ORGANISM: Artificial Sequence
<220> FEATURE:
<223> OTHER INFORMATION: Primer for real-time RT-PCR

<400> SEQUENCE: 10

```
tgtgtaaggc tgcacgagtc                                               20
```

<210> SEQ ID NO 11
<211> LENGTH: 20
<212> TYPE: DNA
<213> ORGANISM: Artificial Sequence
<220> FEATURE:
<223> OTHER INFORMATION: Primer for real-time RT-PCR

<400> SEQUENCE: 11

```
ggcagtagca aaaggcattg                                               20
```

<210> SEQ ID NO 12
<211> LENGTH: 20
<212> TYPE: DNA
<213> ORGANISM: Artificial Sequence
<220> FEATURE:
<223> OTHER INFORMATION: Primer for real-time RT-PCR

<400> SEQUENCE: 12

```
aggcttgaag acccttccat                                               20
```

<210> SEQ ID NO 13
<211> LENGTH: 20
<212> TYPE: DNA
<213> ORGANISM: Artificial Sequence
<220> FEATURE:
<223> OTHER INFORMATION: Primer for real-time RT-PCR

<400> SEQUENCE: 13

```
acaggcagac tggtttcagg                                               20
```

<210> SEQ ID NO 14
<211> LENGTH: 14
<212> TYPE: DNA
<213> ORGANISM: Artificial Sequence
<220> FEATURE:
<223> OTHER INFORMATION: Primer for real-time RT-PCR

<400> SEQUENCE: 14

```
cgcccgtgtt tcca                                                     14
```

<210> SEQ ID NO 15
<211> LENGTH: 19
<212> TYPE: DNA
<213> ORGANISM: Artificial Sequence
<220> FEATURE:
<223> OTHER INFORMATION: Primer for real-time RT-PCR

<400> SEQUENCE: 15

```
tgacccatga cgtacttcc                                                19
```

<210> SEQ ID NO 16
<211> LENGTH: 17
<212> TYPE: DNA
<213> ORGANISM: Artificial Sequence
<220> FEATURE:

-continued

<223> OTHER INFORMATION: Primer for real-time RT-PCR

<400> SEQUENCE: 16 aacgacccctt cattgac                                                17

<210> SEQ ID NO 17
<211> LENGTH: 18
<212> TYPE: DNA
<213> ORGANISM: Artificial Sequence
<220> FEATURE:
<223> OTHER INFORMATION: Primer for real-time RT-PCR

<400> SEQUENCE: 17
ccacgacata ctcagcac                                                18

<210> SEQ ID NO 18
<211> LENGTH: 82
<212> TYPE: PRT
<213> ORGANISM: Unknown
<220> FEATURE:
<223> OTHER INFORMATION: amino acid sequence of mouse nesfatin-1

<400> SEQUENCE: 18

Val Pro Ile Asp Val Asp Lys Thr Lys Val His Asn Thr Glu Pro
1               5                   10                  15

Val Glu Asn Ala Arg Ile Glu Pro Pro Asp Thr Gly Leu Tyr Tyr
                20                  25                  30

Asp Glu Tyr Leu Lys Gln Val Ile Glu Val Leu Glu Thr Asp Pro
                35                  40                  45

His Phe Arg Glu Lys Leu Gln Lys Ala Asp Ile Glu Glu Ile Arg
                50                  55                  60

Ser Gly Arg Leu Ser Gln Glu Leu Asp Leu Val Ser His Lys Val
                65                  70                  75

Arg Thr Arg Leu Asp Glu Leu
                80

<210> SEQ ID NO 19
<211> LENGTH: 69
<212> TYPE: PRT
<213> ORGANISM: Unknown
<220> FEATURE:
<223> OTHER INFORMATION: amino acid sequence of Mutant A90

<400> SEQUENCE: 19

Thr Lys Val His Asn Thr Glu Pro Val Glu Asn Ala Arg Ile Glu
1               5                   10                  15

Pro Pro Asp Thr Gly Leu Tyr Tyr Asp Glu Tyr Ala Lys Ala Ala
                20                  25                  30

Ala Ala Ala Leu Glu Thr Asp Pro His Phe Arg Glu Lys Leu Gln
                35                  40                  45

Lys Ala Asp Ile Glu Glu Ile Arg Ser Gly Arg Leu Ser Gln Glu
                50                  55                  60

Leu Asp Leu Val Ser His Lys Val Arg
                65

<210> SEQ ID NO 20
<211> LENGTH: 67
<212> TYPE: PRT
<213> ORGANISM: Unknown
<220> FEATURE:
<223> OTHER INFORMATION: amino acid sequence of Mutant A91

<400> SEQUENCE: 20

Thr Lys Val His Asn Thr Glu Pro Val Glu Asn Ala Arg Ile Glu
1               5                   10                  15

Pro Pro Asp Thr Gly Leu Tyr Tyr Asp Glu Tyr Ala Ala Ala
                20                  25                  30

Ala Leu Glu Thr Asp Pro His Phe Arg Glu Lys Leu Gln Lys Ala
                35                  40                  45

Asp Ile Glu Glu Ile Arg Ser Gly Arg Leu Ser Gln Glu Leu Asp
                50                  55                  60

Leu Val Ser His Lys Val Arg
                65

<210> SEQ ID NO 21
<211> LENGTH: 64
<212> TYPE: PRT
<213> ORGANISM: Unknown
<220> FEATURE:
<223> OTHER INFORMATION: amino acid sequence of Mutant A92

<400> SEQUENCE: 21

Thr Lys Val His Asn Thr Glu Pro Val Glu Asn Ala Arg Ile Glu
1               5                   10                  15

Pro Pro Asp Thr Gly Leu Tyr Tyr Asp Glu Tyr Ala Ala Leu Glu
                20                  25                  30

Thr Asp Pro His Phe Arg Glu Lys Leu Gln Lys Ala Asp Ile Glu
                35                  40                  45

Glu Ile Arg Ser Gly Arg Leu Ser Gln Glu Leu Asp Leu Val Ser
                50                  55                  60

His Lys Val Arg

<210> SEQ ID NO 22
<211> LENGTH: 20
<212> TYPE: PRT
<213> ORGANISM: Unknown
<220> FEATURE:
<223> OTHER INFORMATION: A synthetic peptide which was the C-terminal
      portion of pladin

<400> SEQUENCE: 22

Ala Asp Ile Glu Glu Ile Arg Ser Gly Arg Leu Ser Gln Glu Leu
1               5                   10                  15

Asp Leu Val Ser His
                20

<210> SEQ ID NO 23
<211> LENGTH: 69
<212> TYPE: PRT
<213> ORGANISM: Unknown
<220> FEATURE:
<223> OTHER INFORMATION: amino acids by MALDI-TOF/TOF with Trypsic
      Peptides

<400> SEQUENCE: 23

Thr Lys Val His Asn Thr Glu Pro Val Glu Asn Ala Arg Ile Glu
1               5                   10                  15

Pro Pro Asp Thr Gly Leu Tyr Tyr Asp Glu Tyr Leu Lys Gln Val
                20                  25                  30

Ile Glu Val Leu Glu Thr Asp Pro His Phe Arg Glu Lys Leu Gln
                35                  40                  45

Lys Ala Asp Ile Glu Glu Ile Arg Ser Gly Arg Leu Ser Gln Glu
                50                  55                  60

```
Leu Asp Leu Val Ser His Lys Val Arg
                65

<210> SEQ ID NO 24
<211> LENGTH: 20
<212> TYPE: PRT
<213> ORGANISM: Unknown
<220> FEATURE:
<223> OTHER INFORMATION: amino acids by MALDI-TOF/TOF with Trypsic
      Peptides

<400> SEQUENCE: 24

Ala Asn Ala Glu Asp Ile Lys Ser Gly Lys Leu Ser Gln Glu Leu
1               5                   10                  15

Asp Phe Val Ser His
                20

<210> SEQ ID NO 25
<211> LENGTH: 78
<212> TYPE: PRT
<213> ORGANISM: Unknown
<220> FEATURE:
<223> OTHER INFORMATION: amino acids recombinant peptide of NUCB1

<400> SEQUENCE: 25

Val Pro Val Asp Arg Ala Ala Pro Gln Glu Asp Ser Gln Ala
1               5                   10                  15

Thr Glu Thr Pro Asp Thr Gly Leu Tyr Tyr His Arg Tyr Leu Gln
                20                  25                  30

Glu Val Ile Asn Val Leu Glu Thr Asp Gly His Phe Arg Glu Lys
                35                  40                  45

Leu Gln Ala Ala Asn Ala Glu Asp Ile Lys Ser Gly Lys Leu Ser
                50                  55                  60

Gln Glu Leu Asp Phe Val Ser His Asn Val Arg Thr Lys Leu Asp
                65                  70                  75

Glu Leu Lys
```

PLASMA ANTI-DIABETIC NUCB2 PEPTIDE (PLADIN) AND USES THEREOF

This application claims benefit of U.S. Ser. No. 61/253,603, filed Oct. 21, 2009 and U.S. Ser. No. 61/159,574, filed Mar. 12, 2009. The contents of these preceding applications are hereby incorporated in their entireties by reference into this application.

FIELD OF THE INVENTION

This invention relates generally to the study of diabetes. In one embodiment, the present invention provides a method of using NUCB2 peptides (e.g. pladin or nestafin-1) to treat diabetes.

BACKGROUND OF THE INVENTION

Diabetes is increasing at an alarming rate worldwide even in the developing countries. The high blood glucose in diabetic patients damages blood vessels, nerves, eyes and kidney, which finally causes severe cardiovascular diseases, neuropathy, blindness and renal failure. Therefore, control of blood glucose is the key battle ground to fight for diabetes.

For type-1 diabetic patients who lack insulin, the administration of insulin before food intake prevents hyperglycemia. For the most diabetic patients classified as type-2 diabetes in which either the body does not produce enough insulin or the cells ignore the insulin, elevated levels of blood glucose are considered responsible for excess complications causing morbidity and mortality. Many drugs have been developed to control blood sugar in type-2 diabetes as classified as following, 1) sulphonylures, which increase insulin release from pancreatic islets; 2) metformin, which acts to reduce hepatic glucose production; 3) glitazones, which are peroxisome proliferator-activated receptor-γ (PPAR-γ) agonists and sensitize insulin receptor downstream signaling; 4) α-glucosidase inhibitors, which interfere with gut glucose absorption; 5) incretins, which are agonists for GLP-1 receptor and promote insulin secretion; 6) DPP-IV inhibitors, which suppress degradation of endogenous GLP-1 and enhance insulin secretion; and finally insulin itself, which suppresses glucose production and augments glucose utilization (Moller, 2001). However, the magic bullet to treat type-2 diabetes has yet to be discovered, since these medicines have limited efficacy.

Studies using mouse mutations have helped to define the regulatory circuits that govern energy expenditure, and to further understand the causes of obesity and diabetes. The well known example is the study of leptin. Mice lacking leptin ($lep^{-/-}$) or leptin receptor ($lepr^{-/-}$) are obese, diabetic, infertile, hyperphagic and hypoactive (Chua et al., 1996).

Brain hypothalamus expressed several secreted molecules that function in regulating feeding behavior. NUCB2/nucleobindin 2 (also called NEFA for DNA binding/EF-hand/acidic protein) is a hypothalamus-secreted protein containing 396 amino acids that is highly conserved in human, mice and rat. Polypeptide encoded by the NEFA gene has a calcium-binding domain (EF domain) and a DNA-binding domain. NEFA has a high homology with nucleobindin and is considered to be a member of the DNA-binding factor called the EF-hand superfamily having reactivity with calcium.

NUCB2 when injected directly into the brain of rats promotes anorexia and decreases body weight. NUCB2 has been postulated to be cleaved posttranslationally by prohormone convertases into an N-terminus-fragment Nesfatin-1 (NEFA/nucleobindin2-encoded satiety- and fat-influencing protein) and two C-terminal peptides, Nesfatin-2 and Nesfatin-3. Nesfatin-1 possesses all of the anorexigenic property of NUCB2. Intracerebroventricular (i.c.v.) or i.p. injection of nesfatin-1 inhibits food intake and thereby reduces body weight. The conversion of NUCB2 into Nesfatin-1 is indispensable for its activity in vivo. Nesfatin-1 is found in discrete nuclei of the hypothalamus where it probably activates a leptin-independent melanocortin pathway. Nesfatin-1 crosses the Blood Brain Barrier (BBB) in both the blood-to-brain and brain-to-blood directions by a nonsaturable system.

NUCB2 is also expressed in the adipocyte cell line 3T3L1 suggesting other functions of Nesfatin-1 outside brain or peripheral source of Nesfatin-1 affecting brain function. Nesfatin-1 in rat stimulates calcium influx and interacts with a G protein-coupled receptor still to be characterized.

Although the plasminogen system is primarily responsible for fibrin degradation, its roles in brain and neurological function have been implicated. Plasminogen and its activators (TPA and uPA) are expressed in developing/adult brains, including hippocampal large pyramidal neurons and dendrites. Plasmin was reported to be involved in the process of hormones derived from the POMC precursor in the intermediate pituitary. Plasminogen was found to affect adipocyte formation (Selvarajan et al., 2001).

SUMMARY OF THE INVENTION

Nesfatin-1 was previously reported as a satiety molecule to suppress food intake via the melanocortin signaling in hypothalamus. Here it was reported that nesfatin-1 improved diabetic symptoms peripherally in db/db mice in addition to its central inhibition of appetite.

Based on a postulation that nesfatin-1 was the putative substrate of plasmin, plasminogen and leptin receptor or leptin gene double deficient mice were generated to investigate the effect of elevated nesfatin-1 in obese and diabetic animals. The double knockouts had significantly higher hypothalamic nesfatin-1, less food intakes and lighter body weights than their counterparties, db/db and ob/ob. The high blood glucose and insulin in db/db were normalized by plasminogen deficiency. Nesfatin-1 was found more in serum than hypothalamus, and always more with freely feeding than fasting. Interestingly, the cerebral TPA was also found lower with freely feeding than fasting, related to the proteolytic inactivation of nesfatin-1. Peripheral nesfatin-1 was also believed to be degraded by plasmin at least in-part, evidenced by the following two findings: one was that intravenous administration of AMCA and aprotinin had similar effects to plasminogen knockout in db/db, and another was that i.v. nesfatin-1 was cleared much slower in $plg^{-/-}$ than $plg^{+/+}$ mice. Peripheral injection of nesfatin-1 significantly reduced blood glucose in db/db. Since the effect of nesfatin-1 was insulin-dependent, it is promising to be developed into a novel therapeutics for type-II diabetes.

The present invention also discloses a naturally occurring 69-amino-acid nucb2 peptide (named as pladin, plasma anti-diabetic nucb2 peptide or plasmin related anti-diabetic nucb2 peptide) elevated in the plasma of plasminogen and leptin receptor or leptin gene double deficient knockout mice was responsible for the anti-diabetic effect of plasminogen deficiency. Intravenous injection of recombinant pladin significantly reduced blood glucose in db/db. The anti-hyperglycemic effect of pladin was time-, dose-, insulin-dependent and peripheral. Using site-directed mutagenesis, plasmin was implicated important for inactivation of pladin. Like nesfatin-1, recombinant Pladin also inhibited appetite centrally. To avoid neuropyschological effects, a long-acting version of pladin without entering brain was created. Pladin as a novel class of insulin helpers may lead to new treatment for type-2 diabetes.

BRIEF DESCRIPTION OF THE FIGURES

Data were presented as means±SEM as indicated in the figure legends. All data were representative of at least three different experiments. Comparisons between individual data points were made using a two-tailed student's t-test. Differences were considered statistically significant when p was less than 0.05.

FIG. 4 shows (a) SDS-PAGE zymography of mouse hypothalamus extracts: control-TPA standard, ff-free feeding, f-fasting; (b) Serum nesfatin-1 in mice; (c) Blood glucose of mice injected with nesfatin-1/saline; (d) The dose-dependent and (e) time-dependent effect of i.v. nesfatin-1; (f) The IGTT in wild-type mice; (g) The effect of nesfatin-1 in the Streptozotocin-induced type-I diabetic C57BL/6J mice, 4 males/group. Data represented the mean±SEM (*, p<0.05, **, p<0.01). Number of mice used showed in parentheses.

FIG. 7 shows that plasminogen deficiency reduced body weight and food intake in db/db and ob/ob mice, normalized blood glucose and serum insulin in db/db mice: (A, C) plg/lepr and (B, D) plg/lep Body weight of mice over 24 weeks on chow diet and their daily food intake at 5, 10, 15 and 20 weeks of age. (E) Fasting blood glucose of mice over ages. (F) Serum insulin of mice at age of 12 weeks. (G) Blood glucose during IP-GTT of mice at age of 16~18 weeks. Data represented the mean±SEM. *, p<0.05, **, p<0.01 compared with obese mice. Number of mice used showed in parentheses.

FIG. 9 shows the structural identification of rPladin: (A) Serum pladin was analyzed with RP-C18-HPLC, as 25 μL sera from free fed wild-type mouse were loaded. (B) The molecular weight of pladin was determined with MALDI-TOF. (C-E) The amino acid sequence of pladin was determined by MALDI-TOF/TOF with trypsic peptides.

DETAILED DESCRIPTION OF THE INVENTION

Figure 1:
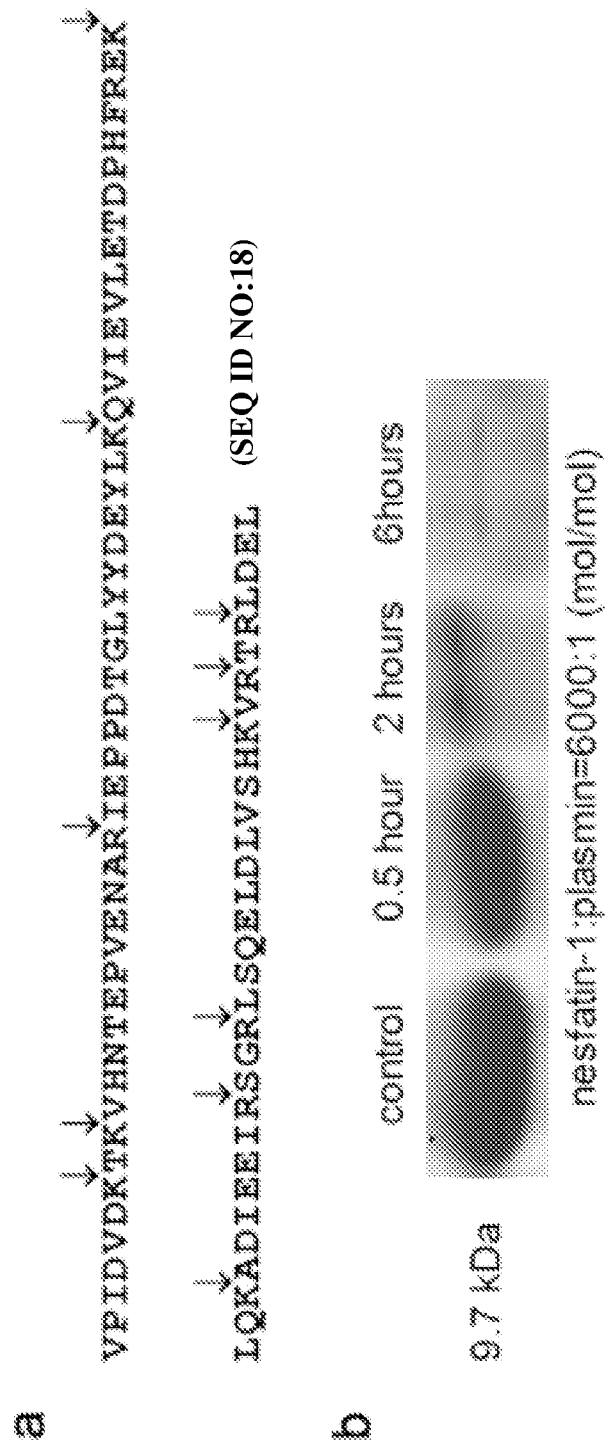
FIG. 1 shows (a) the amino acid sequence of mouse nesfatin-1 (SEQ ID NO: 18). Arrows indicated the putative cleavage sites by plasmin. (b) Nesfatin-1 was completely digested by plasmin within 2 hours.

The following terms shall be used to describe the present invention. In the absence of a specific definition set forth herein, the terms used to describe the present invention shall be given their common meaning as understood by those of ordinary skill in the art.

As used herein, "Pladin" refers to a naturally occurring 69-amino-acid nucb2 peptide (named as pladin, plasma anti-diabetic nucb2 peptide or plasmin related anti-diabetic nucb2 peptide) that is newly discovered in this application.

As used herein, nucleobindin is a class of EF-hand motif containing $Ca^{2+}$-binding protein that has multiple functions. Two nucleobindins have been identified so far, including NUCB1 (or CALNUC, NUC) and NUCB2. As used herein, "NUCB2" refers to nucleobindin 2, also called NEFA (for DNA binding/EF-hand/acidic protein). NUCB1 and NUCB2 are highly homologous with 62% amino acid sequence identity, although they are encoded by two separate and unlinked gene loci. The most characteristic feature of NUCB1 and NUCB2 is the presence of multiple functional domains, including a signal peptide, a leucine/isoleucine rich region, a putative nuclear localization signal and a DNA-binding domain, two $Ca^{2+}$-binding EF-hand motifs, and a leucine zipper region.

The present invention discloses that plasminogen/plasmin directly affects metabolic homeostasis including appetite, body weight and blood sugar with plasminogen deficient db/db or ob/ob mice. More importantly, based on these findings a naturally occurring plasma anti-diabetic nucb2 peptide, pladin, was identified using comparative plasma proteomics. Since pladin is mainly inactivated by plasmin, it is considered to be responsible for the anti-diabetic effect of plasminogen deficiency in db/db mice.

Comparing with all the other anti-hyperglycemic drugs, pladin is certainly a new class of insulin helpers. In the hyperglycemic db/db mice which mimic type-2 diabetes and the glucose infused wild-type animals, a bolus i.v. injection of 10 nmol rPladin would maintain significantly lower levels of blood glucose for 6 hours without any additional administration of insulin. Its action was dose, time and insulin-dependent and peripheral. As a portion of previously identified 82 amino-acid nucb2 anorexigenic peptide, nesfaion-1, the i.v., i.p. and i.c.v. administration of 69 amino-acid rPladin exhibited the same extent of inhibition in food intake as nesfatin-1. Conversely, it is found that i.v. administration of nesfatin-1 reduced blood glucose in db/db mice, similar to rPladin. Nesfatin-1 was postulated based on the putative proteolytic site of prohormone convertases on nucb2. The anti-hyperglycemic effect of nesfatin-1 was overlooked in the previous reports (Folsom et al., 2001; Shimizu et al., 2009), which was probably due to the i.p. administration and the use of non-hyperglycemic animals. Although pladin could affect food intake centrally, its anti-hyperglycemic effect has been demonstrated to be simply peripheral. Caloric restriction and i.c.v. injection of rPladin could not affect blood glucose and insulin in db/db mice. In addition, fasting did not affect the level of blood insulin in db/db mice (data not shown).

The half-life of nesfatin-1 was reported to be 9-10 minutes (Pan et al., 2007; Price et al., 2007). Similarly, it is found that the half-life of rPladin in circulation was also less than 10 minutes (data not shown). However, its anti-hyperglycemic effect lasted longer than 6 hours (FIG. 13A), suggesting that its intracellular signaling would be long lasting. Although the intracellular mechanism of ant-hyperglycemic pladin is yet unknown, it surely interacts with the signaling pathways of insulin. In an in vivo experiment, it is found that the anti-hyperglycemic effect of rPladin was prevented by the PPAR-γ antagonist (GW9662) and the AMPK inhibitor (Compound C), two well-known elements of insulin signaling. Consistent to the postulation that pladin was mainly inactivated by plasmin, the results of acetylation and Ala substitution on Lys and Arg residues indicated that the half-life of pladin in circulation could be significantly prolonged by the avoidance of plasmin proteolysis. Additionally, the conjugate of albumin could significantly prevent pladin from extravascular exclusion, although it had no effect on the proteolytic inactivation. In the experiments presented herein, the active duration of i.v. rPladin was increased up to 36 hours using acetylation and conjugation, which could be developed into a long-lasting version of pladin with recombinant technologies.

Moreover, since AMCA (tranexamic acid) is clinically available to reduce blood loss in surgery and effectively mimics the effect of pladin in hyperglycemic db/db mice (FIG. 12A-E), AMCA was used successfully to treat post-surgical hyperglycemia. Ten mg/kg of AMCA was given i.v. BID to four post-surgical patients whose blood glucoses were 10-12 mmol/L. The anti-hyperglycemic effect was seen immediately after the treatment, evidenced by the level of blood glucose dropping to 6.8-9.2 mmol/L.

Although pladin is found as a natural substance in circulation, it is unclear how it is processed from its precursor nucb2 and secreted to blood. The nucb2 mRNA and related proteins were found in gastric oxyntic mucosa, paraventricular and supraoptic nuclei of hypothalamus and pancreatic islets (Gonzalez et al., 2009; Oh-I et al., 2006; Stengel et al., 2009), and down-regulated in hypothalamus (Oh-I et al., 2006) when the animals were fasting. Consistent to these previous findings, it is observed that fasting significantly reduced the plasma levels of pladin in wild-type and db/db mice compared with freely feeding (FIG. 12G), which indicated a physiological role of pladin in energy haemostasis. Parallel to the action of insulin and consistent to its dependence of insulin, pladin acts closely on both glucose metabolism and food intake, suggesting its importance in metabolic control of the body. Therefore, further studies on pladin would lead to better understanding of energy metabolism and a novel treatment for type-2 diabetes.

The present invention provides a method of treating a subject having diabetes, comprising the step of administering to the subject a composition comprising an effective amount of a polypeptide such as nesfatin-1, pladin (plasma anti-diabetic nucb2 peptide), or a functional equivalent thereof. In general, the composition can be administered intravenously, subcutaneously, or orally. In one embodiment, the polypeptide can be derived from human or rodent. Functional equivalents of nesfatin-1 or pladin are those that can manifest the desired activities of nesfatin-1 or pladin. Examples of such functional equivalents include, but are not limited to, a homologous peptide of nesfatin-1, a homologous peptide of pladin, or a derivative thereof such as a motif or fragment similar to SEQ ID NO:24. Using standard methodology in the art, one of ordinary skill in the art would readily determine a portion or domain of nesfatin-1 or pladin that manifests the desired activities. For example, truncated nesfatin-1 or pladin, or fragments of nesfatin-1 or pladin can be generated by standard recombinant techniques and tested in the assays described herein to determine their anti-diabetic activities. Moreover, recombinant mutants of nesfatin-1 or pladin can also be tested. The present method covers the use of molecules which contain full-length, a fragment thereof, or a mutant nesfatin-1 or pladin. In one embodiment, the pladin, nesfatin-1, or functional equivalent thereof, comprise a sequence of any one of SEQ ID NOs:18-25. In another embodiment, the pladin has a mutation at $Arg^{13}$ or $Lys^{28}$. In yet another embodiment, the polypeptide is a conjugated molecule having increased molecular weight. One of ordinary skill in the art would readily construct a higher molecular weight nesfatin-1, pladin, or a functional equivalent thereof by conjugating with a number of carriers or proteins well-known in the art such as albumin, immunoglobulin, Fc, Apolipoprotein, etc. Such conjugated nesfatin-1 or pladin would reduce blood glucose without penetration of blood-brain barrier. Furthermore, the polypeptide can be modified, e.g. the pladin can be modified as an acetylated molecule.

The present invention also provides a method for reducing triglyceride, total cholesterol or LDL in blood, comprising the step of administering to the subject a composition comprising an effective amount of a polypeptide such as nesfatin-1, pladin (plasma anti-diabetic nucb2 peptide), or a functional equivalent thereof. Description and examples of applicable polypeptides have been discussed above.

The above methods would be useful for treating a subject having type II diabetes. In another embodiment, the method would be useful for treating a subject having type I diabetes, wherein treatment for type I diabetes would further comprise the step of administering insulin to the subject. In another embodiment, the above method also results in reduced body weight or reduced food intake in the subject.

The present invention also provides a method of treating a subject having diabetes, comprising the step of administering to a subject an effective amount of a plasmin inhibitor, wherein the plasmin inhibitor would increase peripheral nesfatin-1 or pladin (plasma anti-diabetic nucb2 peptide). Examples of plasmin inhibitors include, but are not limited to, aprotinin, AMCA (tranexamic acid), EACA (epsilon-amino-caproic acid) or their analogues.

The present invention also provides a method for reducing triglyceride, total cholesterol or LDL in blood, comprising the step of administering to a subject an effective amount of a plasmin inhibitor, wherein the plasmin inhibitor would increase peripheral nesfatin-1 or pladin (plasma anti-diabetic nucb2 peptide). Examples of plasmin inhibitor include, but are not limited to, aprotinin, AMCA (tranexamic acid), EACA (epsilon-amino-caproic acid) or their analogues.

The present invention also provides uses of a polypeptide for the preparation of medicament for the treatment of diabetes, or for reducing triglyceride, total cholesterol or LDL in blood. Examples of such polypeptide have been discussed above. Such uses would be useful for treating type II diabetes, or treating type I diabetes together with the administration of insulin.

The present invention also provides uses of a plasmin inhibitor for the preparation of medicament for the treatment of diabetes, or for reducing triglyceride, total cholesterol or LDL in blood. Examples of plasmin inhibitors include, but are not limited to, aprotinin, AMCA (tranexamic acid), EACA (epsilon-amino-caproic acid) or their analogues.

The present invention also provides a transgenic diabetic or obese rodent comprising homozygous plasminogen gene disruption, wherein the transgenic rodent exhibits reduced body weight or reduced blood glucose as compared to a diabetic or obese rodent not having the plasminogen gene disruption. In one embodiment, the transgenic rodent further comprises homozygous leptin gene disruption or homozygous leptin receptor gene disruption. In one embodiment, the transgenic rodent is a mouse. Such transgenic animals would be useful in a number of studies such as drug screening, clearance studies for nesfatin-1 or pladin, etc.

The present invention also provides a method of screening for an agent that would increase peripheral or brain nesfatin-1 or pladin, comprising the steps of: (i) administering a candidate agent to a subject; (ii) obtaining blood samples or brain tissue samples from the subject; and (iii) determining the amount of nesfatin-1 or pladin in the samples, wherein an increased amount of nesfatin-1 or pladin as compared to that in samples obtained from subject treated with a control substance would indicate that the candidate agent would increase peripheral or brain nesfatin-1 or pladin. In one embodiment, the subject in the screening method is the transgenic rodent described above. In one embodiment, the amount of nesfatin-1 or pladin can be determined by a HPLC assay as described herein. In another embodiment, the amount of nesfatin-1 or pladin can be determined by a number of assays that utilize anti-nesfatin-1 or pladin antibodies (e.g. ELISA assay).

The present invention also provides a recombinant pladin (plasma anti-diabetic nucb2 peptide), or a functional equivalent thereof. In one embodiment, the pladin or a functional equivalent thereof comprises a sequence of any one of SEQ ID NOs:19-25. In another embodiment, the pladin has a mutation at $Arg^{13}$ or $Lys^{28}$.

Throughout this application, various references or publications are cited. Disclosures of these references or publications in their entireties are hereby incorporated by reference into this application in order to more fully describe the state of the art to which this invention pertains.

The invention being generally described, will be more readily understood by reference to the following example which are included merely for purpose of illustration of certain aspects and embodiments of the present inventions, and are not intended to limit the invention.

EXAMPLE 1

Nesfatin-1 Mediates the Effects of Plasminogen in Obese and Diabetic Animals

Nesfatin-1, a postulated secreted fragment of NUCB2, has been recently identified as an anorexigenic factor associated with melanocortin signaling in hypothalamus. The intracerebroventricular (i.c.v.) or i.p. injection of nesfatin-1 inhibits food intake and thereby reduces body weight. Carefully examining the amino acid sequence of nesfatin-1, it is highly conserved from mouse to human and has several putative cleavage sites by plasmin (FIG. 1a). Therefore, it was postulated that nesfatin-1 could mediate the effect of plasminogen in obese and diabetic animals.

To prove this assumption, recombinant nesfatin-1 was expressed and purified from genetically engineered E. coli. It was then incubated with plasmin and rapidly degraded as expected (FIG. 1b). Intriguingly, hypothalamic nesfatin-1 was found significantly less in $plg^{+/+}lepr^{-/-}$ than their non-obese littermates included $plg^{-/-}lepr^{-/-}$ (FIG. 2a), suggesting at least in-part plasminogen/plasmin was accounted for the decrease in nesfatin-1. The recovery of hypothalamic nesfatin-1 in $plg^{-/-}lepr^{-/-}$ was consistent to its normalization in food intake and body weight. Fasted mice always had less nesfatin-1 in hypothalamus than their freely feeding counterparties (FIG. 2b). Furthermore, plasminogen deficiency provided a unique approach to study the chronic effect of elevated nesfatin-1 in hyperphagic obese animals, which was impossible for the i.c.v. or i.p. administration due to the short half-time of nesfatin-1. Consequently, agrp and npy were found reduced in $plg^{-/-}lepr^{-/-}$, while pomc was elevated compared with $plg^{+/+}lepr^{-/-}$ (FIG. 3), contradicting to the previous report that i.c.v. nesfatin-1 didn't alter the expression of pomc, npy and agrp. Consistent to the present finding, the same group reported the up-regulation of pomc by i.p. nesfatin-1 in NTS recently.

Figure 2:
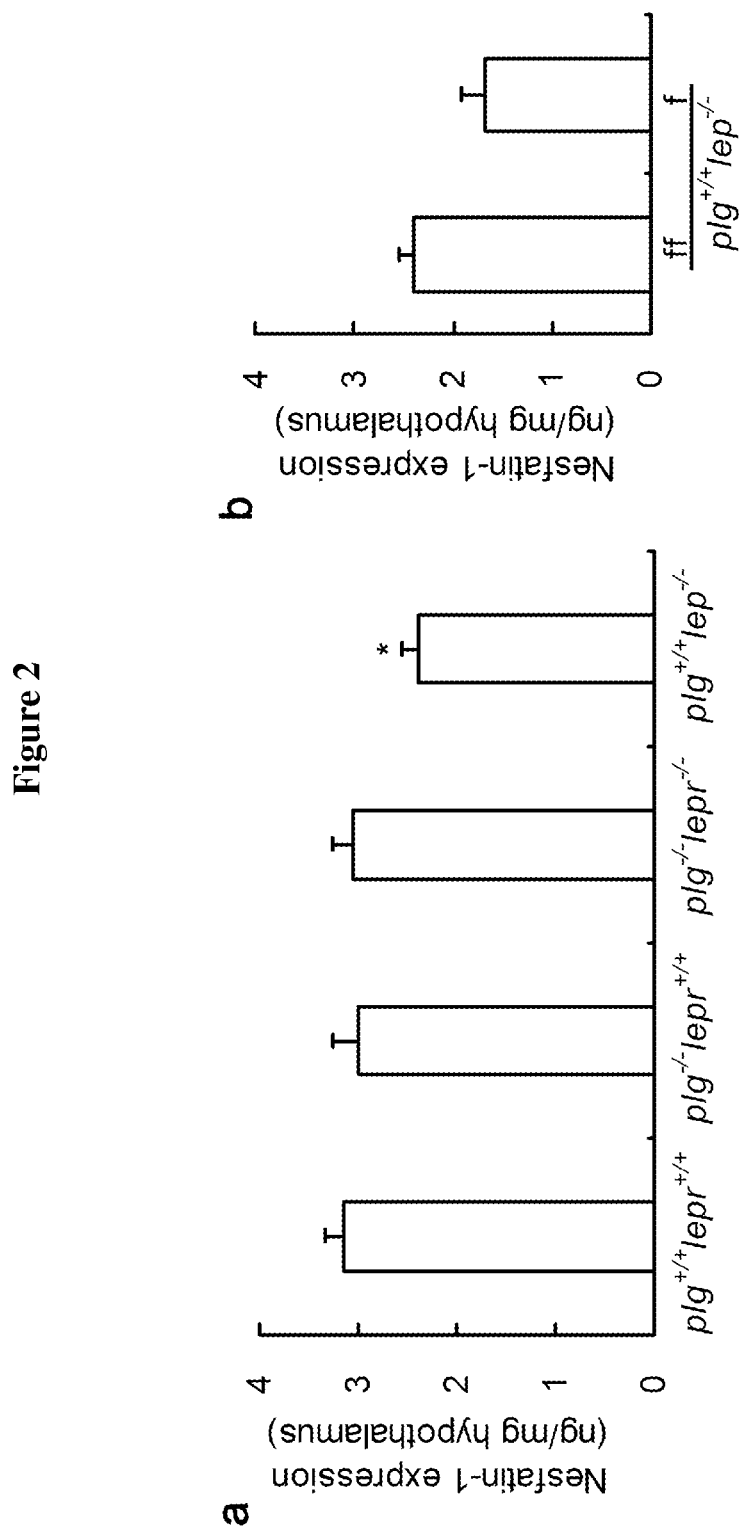
FIG. 2 shows the hypothalamic nesfatin-1 measured by HPLC in (a) each genotype; (b) with fasting and freely feeding. Data represented the mean±SEM for samples in quadruplicate (three mouse hypothalami per sample).
Figure 3:
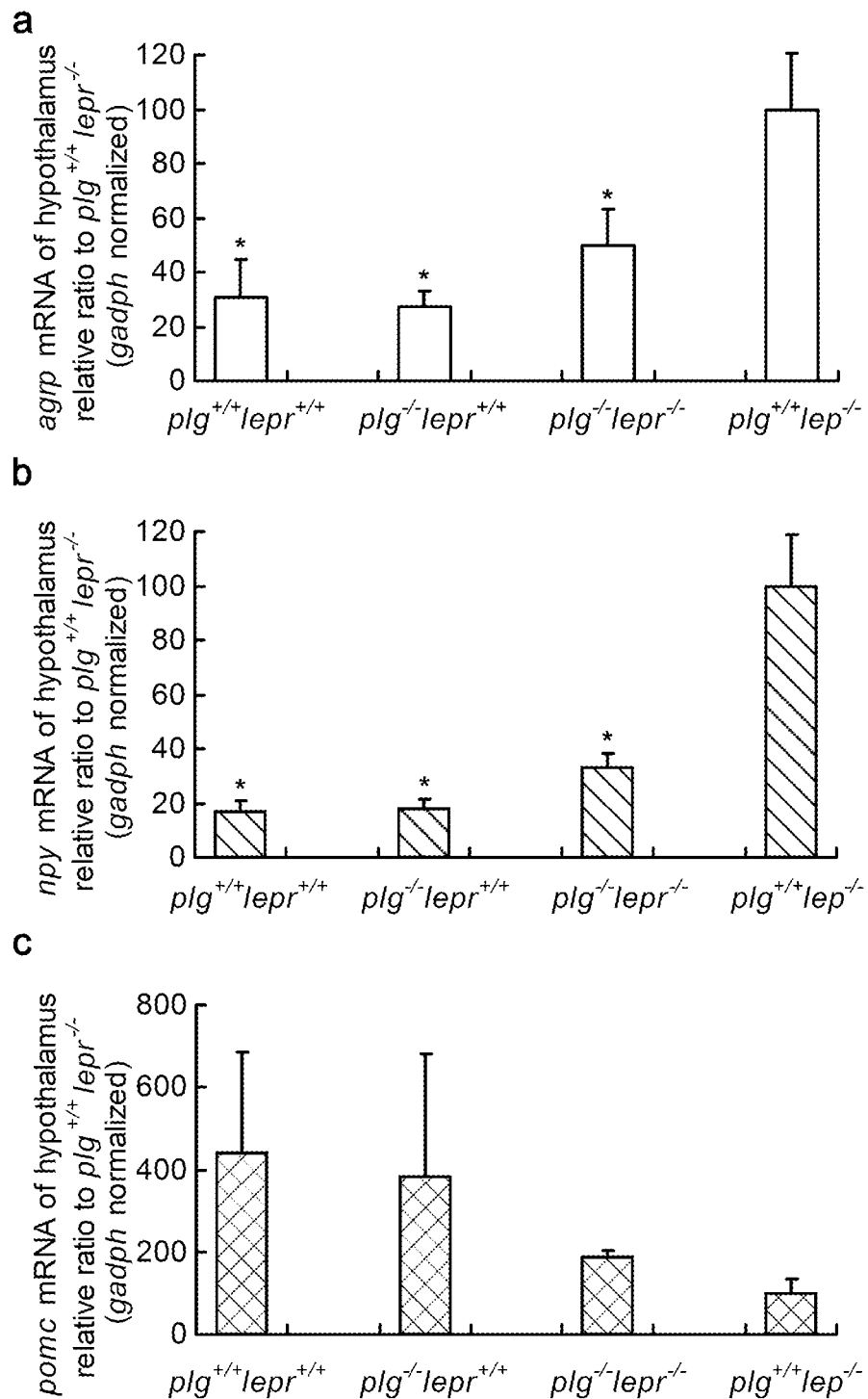
FIG. 3 shows hypothalamic mRNA encoding neuropeptides in $plg^{-/-}lepr^{-/-}$ mice versus littermates including $plg^{+/+}lepr^{-/-}$. The mRNA Expression was normalized to gadph. (a) agrp, (b) npy and (c) pomc, all measured by quantitative real-time PCR. Data represented the mean±SEM for samples in triplicate.

Logically, the proteolytic reduction in nesfatin-1 requires plasmin generation. Indeed, the activity of tissue plasminogen activator (TPA) was increased in hypothalamus from freely feeding to fasting (FIG. 4a), well correlated to the changes in hypothalamic nesfatin-1 (FIG. 2). For the first time, the TPA/plasminogen system was indicated to be involved in the feeding behavior, which was previously suggested to be involved in the learning process. It is well known that feeding can facilitate learning in animals. Nesfatin-1 appears to connect these two important brain functions.

Amazingly as described above, the diabetic symptoms of db/db mice were essentially eliminated in $plg^{-/-}lepr^{-/-}$, which couldn't be possibly explained by the anorexigenic effect of nesfatin-1. The db/db mice with fasting, caloric restriction or i.c.v. injection of nesfatin-1 had little diabetic improvement (data not shown), suggesting that the anti-diabetic effect by plasminogen deficiency would be peripheral rather than neurological. The i.v. administration of 100 µg nesfatin-1 significantly reduced blood glucose in freely fed db/db, but not in fasted db/db and lean wild-type mice (FIG. 4c). This anti-diabetic effect was dose- and time-dependent (FIG. 4d, e). Although the half-life of nesfatin-1 was 10 minutes in circulation, its effect lasted >6 hours, suggesting an enduring intracellular mechanism. During IGTT using wild-type mice, 100 µg nesfatin-1 significantly enhanced the uptake of blood sugar with i.v. injection of 1.5 g/kg glucose, but not 1 g/kg (FIG. 4f). Because nesfatin-1 only reduced blood glucose at the high dose inducing insulin secretion, its effect would be insulin-dependent. Indeed, in the Streptozotocin-induced type-I diabetic mice, the blood glucose decreased only when nesfatin-1 was injected with s.c. insulin (FIG. 4g).

Zymography Assay for the Activity of Tissue Plasminogen Activator (TPA) in Hypothalamus Zymography was used to determine the activity of TPA in hypothalamus as described previously[2]. Hypothalamus isolated from mouse with or without fasting was homogenized and centrifuged. Samples normalized by equal quantity of proteins were mixed with the sample buffer and loaded onto 10% SDS-polyacrylamic gel containing 3 mg/ml casein and 4.5 mg/ml plasminogen. Human TPA 0.1 ng (Genentech, San Francisco, Calif.) was used as a positive control. Following electrophoresis, the gels were soaked in a renature buffer (0.02% NaN3, 200 mM NaCl, 50 mM Tris-HCl, 2.5% Triton X-100, pH 8.3) for 30 minutes at room temperature, and then incubated in the developing buffer (0.02% NaN3, 200 mM NaCl, 50 mM Tris-HCl, pH 8.3) at 37° C. for 18 hours. To visualize the lysis band of TPA, the gels were stained with Coomassie Brilliant Blue R-250 and then destained until clear bands appeared on the blue background.

HPLC Assay for Serum Nesfatin-1

Hypothalamus in acetic acid supplemented with protease inhibitor cocktail tablets (Roche, Indianapolis, Ind.) was homogenized, sonicated and heated at 95° C. for 15 minutes. The samples were then centrifuged at 13,200 rpm at 4° C. for 30 minutes. The supernatants were finally collected as their protein contents were determined by the Bradford assay (Thermo-Fisher Sci. Rockford, Ill.). Mouse serum was freshly prepared by drawing blood through ophthalmectomy. About 100 mg hypothalamic total proteins or 25 µL serum were analyzed with Waters Delta 600E/2487/717 HPLC system using an analytical C18 reverse phase column (4.6×250 mm/5 µm, Hambon, Zhangjiagang, CN). Nesfatin-1 was eluted with a linear gradient from 20%-40% solvent B (solvent A: water with 0.1% trifluoroacetic acid, solvent B: acetonitrile with 0.1% trifluoroacetic acid) for 20 minutes at the flow rate of 1 ml/minute. The purified nesfatin-1 was used as the standard to determine the retention time and plot the standard curve. The fraction collected at the retention time was sent for the mass spectrometry analysis.

Streptozotocin-Induced Type-I Diabetic Mice

Male C57BL/6J mice (10 weeks) were given intraperitoneal injections of Streptozotocin (STZ) in sodium citrate (pH 4.5) on two consecutive days (100 mg/kg/day). Blood glucose was measured by tail vein sampling using the glucose oxidase enzymatic test. Diabetes was defined as a morning blood glucose reading of >16 mM after STZ. When blood glucose levels exceeded 30 mM, diabetic mice were given 16 ng of porcine insulin (Wangbang, Xuzhou, CN) immediately to prevent the blood glucose being dangerous every second day to prevent weight loss while maintaining blood glucose levels within the hyperglycemic range (16-30 mM). Nesfatin-1 (100 µg/mouse) was i.v. injected either alone or combined with s.c. insulin (2 ng/mouse) to STZ-induced type-I diabetic mice.

EXAMPLE 2

The Effect of Intravenous Injection of Plasmin Inhibitor on Blood Nesfatin-1

Figure 5:
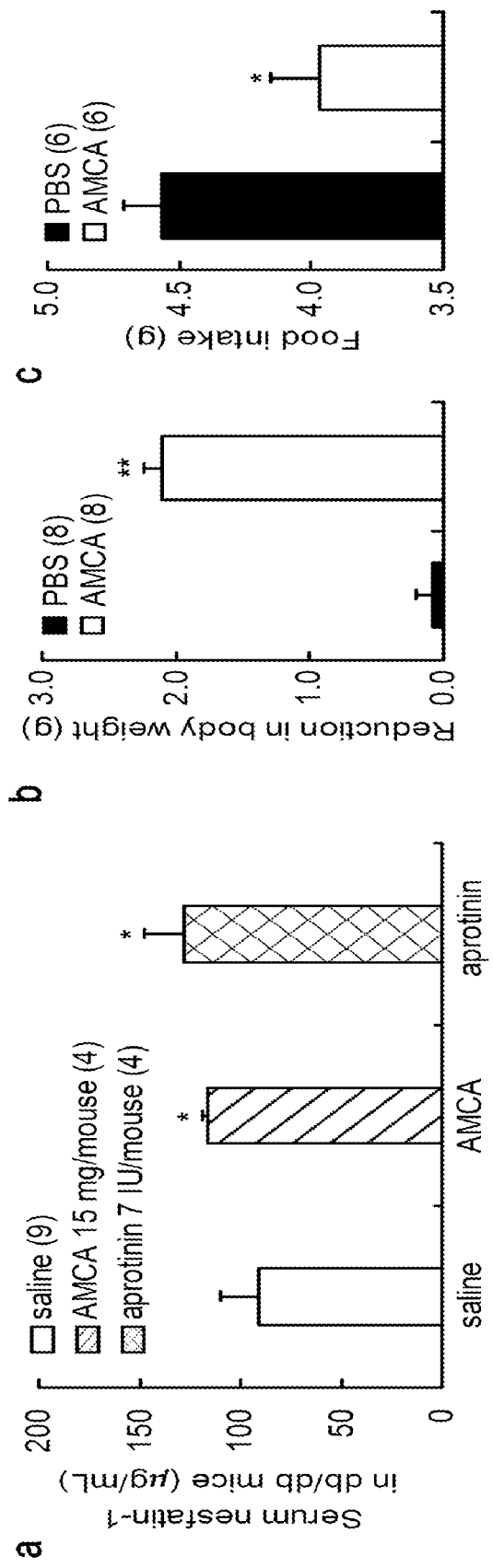
FIG. 5 shows (a) serum nesfatin-1 in db/db at 30 minutes after i.v. AMCA and aprotinin. Lower nesfatin-1 in "saline" than "ff db/db" (FIG. 3b) was due to blood dilution after injection. (b) Reduction in body weight after a 3-day i.v. AMCA (15 mg/day); (c) Food intake at day 3 during a 3-day i.v. AMCA (15 mg/day). Number of mice used showed in parentheses.

It is unknown how nesfatin-1 is cleared from circulation. The tiny amount of plasmin generation in periphery was previously reported and confirmed in the study (data not shown). AMCA and aprotinin, two inhibitors of plasmin, was i.v. injected to db/db. The reduction in food intake and body weight was seen while circulating nesfatin-1 was increased (FIG. 5). The i.v. nesfatin-1 also cleared much slower in $plg^{-/-}$ than $plg^{+/+}$ (data not shown). Therefore, peripheral nesfatin-1 was believed at least partially to be degraded by plasmin. Consistent to the report that nesfatin-1 penetrated BBB without saturation, the anorexigenic effect of AMCA suggested that peripheral nesfatin-1 was at least in-part of the source of cerebral nesfatin-1. Since nesfatin-1 was found to affect rats neuropsychologically as evidenced by increasing anxiety and fear-related behaviors, albumin-nesfatin-1 fusion protein were made effectively reducing blood glucose without entering the brain (data not shown).

For the first time, it was found that TPA/plasminogen directly affects the homeostasis of energy expenditure including appetite, body weight and blood sugar through its proteolytic inactivation of nesfatin-1, although it was found to affect adipocyte differentiation previously. More importantly, the data presented herein demonstrate the anti-diabetic effect of peripheral nesfatin-1, which could lead to a novel treatment for type-II diabetes.

EXAMPLE 3

Quantitative PCR Assay for Neuropeptides

The neuropeptide mRNA was measured using quantitative PCR (q-PCR), using CFX96™ Real-Time System (Bio-Rad, Hercules, Calif.) and the SYBR Green I detection method. Briefly, hypothalamic tissues from 24-hour fasted mice were homogenized, and total RNA was extracted using RNAiso Reagent (TaKaRa, Dalian, CN) and then reversed to single-strand cDNA. The relatively expression of neuropeptide mRNA was determined using the standard curves of hypothalamic cDNA, and adjusted for total RNA contents with gadph RNA by qPCR. Primers for real-time RT-PCR were used as follows: agrp forward primers: 5'-TGT GTA AGG CTG CAC GAG TC (SEQ ID NO:10); agrp reverse primers: 5'-GGC AGT AGC AAA AGG CAT TG (SEQ ID NO:11); agrp Tm: 61° C.; npy forward primers: 5'-AGG CTT GAA GAC CCT TCC AT (SEQ ID NO:12); npy reverse primers: 5'-ACA GGC AGA CTG GTT TCA GG (SEQ ID NO:13); npy Tm: 61° C.; pomc forward primers: 5'-CGC CCG TGT TTC CA (SEQ ID NO:14); pomc reverse primers: 5'-TGA CCC ATG ACG TAC TTC C (SEQ ID NO:15); pomc Tm: 58° C.; gadph forward primers: 5'-AAC GAC CCC TTC ATT GAC (SEQ ID NO:16); gadph reverse primers: 5'-TCC ACG ACA TAC TCA GCA C (SEQ ID NO:17); gadph Tm: 60° C. All the samples were run in triplicate, and the results were averaged.

EXAMPLE 4

Immunohistochemistry of AgRP on Hypothalamus

Figure 6:
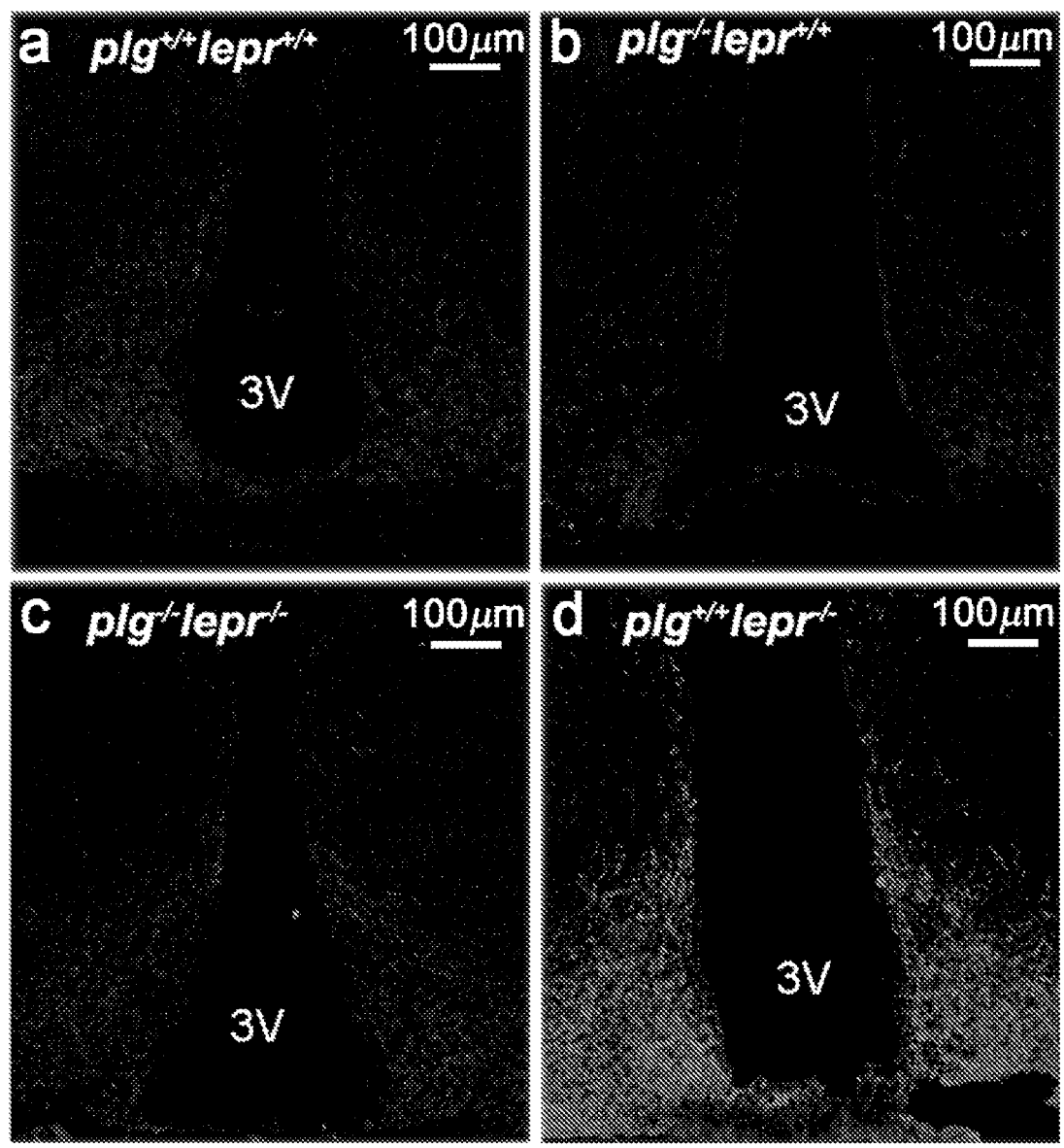
FIG. 6 shows immunohistochemistry of AgRP in arcuate of (a) $plg^{+/+}lepr^{+/+}$; (b) $plg^{-/-}lepr^{+/+}$; (c) $plg^{-/-}lepr^{-/-}$; and (d) $plg^{+/+}lepr^{-/-}$.

After 48-hour fasting, mouse was deeply anesthetized with sodium pentobarbital and transcardially perfused with 20 ml saline, followed by 50 ml of 4% paraformaldehyde in PBS (pH7.4). The brain was removed and post fixed overnight, then stored in PBS with 30% sucrose. To measure the immunofluorescence of AgRP, cryostat sections (20 μm thick) were post fixed with paraformaldehyde, incubated with 1% BSA in PBS for 20 minutes, and then with rabbit anti-AgRP antibody (1:4000, Phoenix Pharmaceuticals, Burlingame, Calif.) in the same solution for 1 days at 4° C. After being washed three times in PBS, the sections were incubated with Cy2-conjugated goat anti-rabbit IgG (1:250, Jackson, West Grove, Pa.) for 2 hours at room temperature, and then washed three times in PBS, mounted and cover-slipped with the buffered glycerol (pH8.5). As shown in FIG. 6, The hypothalamic agrp and npy were found reduced in $plg^{-/-}lepr^{-/-}$, while pomc was elevated compared with $plg^{++}lepr^{-/-}$.

EXAMPLE 5

HPLC Screening Assays for Substances that would Increase Peripheral or Brain Nesfatin-1

Blood samples or brain tissue samples can be taken from mice injected with various substances (such as chemical compounds, proteins, peptides or nucleic acids), and then applied to HPLC as described above. The amount of nesfatin-1 in the sample can then be measured and recorded. In one embodiment, when nesfatin-1 in the sample is found to be 20% higher than that of mice injected with saline, the substance injected in the mice would be selected as an agent for increasing peripheral or brain nesfatin-1.

EXAMPLE 6

Use of Plasmin or Plasminogen Activators to Inactivate Nesfatin-1

In one embodiment, plasmin or plasminogen activator (such as tissue plasminogen activator, urokinase-type plasminogen activator, streptokinase or staphylokinase) at the dose higher than 5 mg per patient per day can be i.v. administrated to patients. The blood or brain nesfatin-1 would be decreased or inactivated. The patient would have an increase in food intake, appetite, blood glucose, or body weight.

EXAMPLE 7

Injection of Nesfatin-1 Significantly Reduced Triglyceride, Total Cholesterol and LDL but not HDL in Blood One hundred ug Nesfatin-1 was injected into the tail vein of ob/ob mice. Blood samples were taken 3 hours after the injection for lipid analysis. Triglyceride, total cholesterol and LDL were significantly reduced by the injection of nesfatin-1, while HDL was unaffected.

EXAMPLE 8

Anti-Diabetic Effect of Nesfatin-1 is Mediated by PPAR-Gamma and AMPK

GW9662, a PPAR-gamma irreversible inhibitor, was i.v. injected into the tail vein of db/db mice at the dose of 0.45 μg per gram body weight. After 30 minutes, 100 ug Nesfatin-1 was injected into the tail vein of db/db mice. Blood glucose was measured in 6 hours.

No reduction in blood glucose was found in mice injected with GW9662 prior to the injection of nesfatin-1. In contrast, without pre-treatment of GW9662, nesfatin-1 significantly reduced blood glucose in db/db mice (see above). Therefore, GW9662 fully inhibited the anti-diabetic effect of nesfatin-1 in db/db mice, suggesting that PPAR-gamma mediates the effect of nesfatin-1.

Compound C, a 5'-AMP-activated protein kinase (AMPK) specific inhibitor, was intraperitoneally injected to db/db mice at the dose of 20 mg per kg body weight. Subsequently, 100 ug Nesfatin-1 was injected into the tail vein of db/db mice. Blood glucose was measured in 6 hours.

No reduction in blood glucose was found in mice injected with Compound C prior to the injection of nesfatin-1. In contrast, without pre-treatment of Compound C, nesfatin-1 significantly reduced blood glucose in db/db mice. Therefore, Compound C fully inhibited the anti-diabetic effect of nesfatin-1 in db/db mice, suggesting that AMPK also mediates the effect of nesfatin-1.

EXAMPLE 9

Nesfatin-1 Analogues with Larger Molecular Weights

Since nesfatin-1 was found to affect rats neuropsychologically as evidenced by increasing anxiety and fear-related behaviors, larger-molecular-weight nesfatin-1 analogues that effectively reduce blood glucose but is prevented from penetrating blood-brain barrier (BBB) were made as follows. In one embodiment, a chemical conjugate of nesfatin-1 and albumin can be made.

Synthesis of Albumin-Nesfatin-1 Conjugate 20 mg nesfatin-1 (0.002 mmol) was solved in 5 mL 0.1M PBS buffer (pH7.2) to give a clear solution, 4 mg (0.01 mmol) SMPT (4-succinimidyloxycarbonyl-a-methyl-[2-pyridylditho]toluene]) solved in acetonitrile with concentration 10 mg/ml was added drop-wisely into nesfatin-1 solution with rapid stiffing. The mixture was kept stiffing overnight at room temperature and then dialyzed against 0.1M PBS and 10 mM EDTA to remove excess reagent and to exchange the buffer. 84 mg bovine albumin (0.0013 mmol) solved in 8 mL PBS-EDTA solution was then added to the modified nesfatin-1 solution, the conjugation was quantified to measure the leaving group pyridine-2-thione, which has an absorption maximum at 343 nm, using a spectrophotometer. After 48 hours reaction at room temperature, the excess pyrinde-2-thione groups were quenched with 0.4 mg cystein. The conjugate was obtained after the size exclusion chromatography to remove the free nesfatin-1 and the modified nesfatin-1. During the whole reaction, 10% SDS-PAGE Gel was used to monitor and evaluate the conjugate reaction.

Even though the SMPT was in 4 fold molar excess, about 20-30% free nesfatin-1 was detected by analytical HPLC in the modified solution. The conjugate reaction was mostly stopped after 48 hours, since the absorption at 343 nm had not obvious increment. SDS-Page gel also showed there has not too much change after 48 hours reaction. The yield of the albumin-nesfatin-1 conjugate is about 50-60% estimated from the gel.

EXAMPLE 10

Large Molecular Weight Nesfatin-1 Analogue Reduces Blood Glucose without Penetration of Blood-Brain Barrier The albumin-nesfatin-1 conjugate was labeled with $I^{125}$ and intravenously injected to db/db mice and C57Bl/6J mice. Brain samples were taken at 0, 3, 5, 10, 30 and 60 minutes after the injection to measure its radioactivity using a gamma counter. Equal amount of radioactive $NaI^{125}$ was used as positive control.

The conjugate of albumin-nesfatin-1 (250 µg) was injected into the tail vein of db/db mice. Blood glucose was measured in 6 hours. No radioactivity was detected in the mouse brain injected with $I^{125}$-labeled albumin-nesfatin-1 conjugate at any time points. In contrast, the radioactivity was detected in the mouse brain injected with $NaI^{125}$ at 3-30 minutes and decreased over time. Thus, these results indicated that the albumin-nesfatin-1 conjugate did not penetrate blood-brain barrier to enter the brain from circulation. In contrast, iv injection of conjugate of albumin-nesfatin-1 significantly reduced blood glucose in db/db mice with 6 hours.

EXAMPLE 11

Experiment Procedures

Animal Care

Lepr$^{+/-}$ mice in C57BLKS/J, plasminogen heterozygous (plg$^{+/-}$) and lep$^{+/-}$ in C57Bl/6J were purchased from Jackson Laboratory (Bar Harbor, Me.). All animals were kept under specific pathogen-free conditions with lab chow available ad libitum (freely feeding) in a 12-hour light/dark cycle. All procedures in animal experiments were in accordance with US National Institutes of Health animal care guidelines and were conducted with the approval from the Animal Study Committee.

Generation of plg$^{-/-}$lepr$^{-/-}$ Mice and Genotyping plg$^{+/-}$ mice were crossed with lepr$^{+/-}$ and lep$^{+/-}$ to generate plg$^{+/-}$ lepr$^{+/-}$ and plg$^{+/-}$ lep$^{+/-}$ mice. These mice were then used to produce plasminogen deficient in db/db and ob/ob mice, plg$^{-/-}$lepr$^{-/-}$ and plg$^{-/-}$lep$^{-/-}$.

Mice (lepr wild-type, lepr mutant, lep wild-type, lep-mutant, plasminogen wild-type, plasminogen mutant) were genotyped by PCR using genomic DNA isolated from tail tips. The primer sequences were used as following, lepr-wild-type-F: 5'-TAC ATT TTG ATG GAG GG-3'(SEQ ID NO:1); lepr-mutant-F: 5'-TAC ATT TTG ATG GAG GT-3 (SEQ ID NO:2); lepr-same-R: 5'-GGA ATC TAA TAT GGA AG-3' (SEQ ID NO:3); lep-wild-type-F: 5'-TGA CCT GGA GAA TCT CC-3'(SEQ ID NO:4); lep-mutant-F: 5'-TGA CCT GGA GAA TCT CT-3'(SEQ ID NO:5); lep-same-R: 5'-CAT CCA GGC TCT CTG GC-3'(SEQ ID NO:6); plg-wild-type-F: 5'-TGT GGG CTC TAA AGA TGG AAC TCC-3'(SEQ ID NO:7); plg-mutant-F: 5'-GTG CGA GGC CAG AGG CCA CTT GTG TAG CG-3'(SEQ ID NO:8); plg-same-R: 5'-TGT GGG CTC TAA AGA TGG AAC TCC-3'(SEQ ID NO:9).

Body Weight, Food Intake, Fasting Blood Glucose and Serum Insulin Tests

At weaning, mice were placed on the standard lab chow and followed for at least 24 weeks. As body weight was measured weekly, the chow consumed was recorded daily and averaged over the whole week at the age of 5, 10 and 15 weeks. Mice were fasted for 18 hours at 8, 16 and 24 weeks old before taking blood samples from tail vein to measure the fasting blood glucose using a glucose meter (Roche, Indianapolis, Ind.). The levels of serum insulin were measured by ELISA (ALPCO, Salem, N.H.). At least 8 mice per group were studied in both sexes of each genotype, plg$^{+/+}$lepr$^{-/-}$, plg$^{-/-}$lepr$^{-/-}$, plg$^{+/+}$lepr$^{+/+}$, and plg$^{-/-}$lepr$^{+/+}$.

Glucose Tolerance Test (GTT)

In the intraperitoneal (i.p.) glucose tolerance test (IP-GTT) (Zheng et al., 2004), 12-week old mice were placed in clean cages without food at 4 pm on the day prior to the experiment. At 10 am the following day, the mice were injected intravenously with 1 mg glucose per gram of body weight. Blood glucose was measured immediately before and at 10, 20, 30, 60, 90, 120 and 180 minutes after the injection of glucose.

In the intravenous (i.v.) glucose tolerance test (IV-GTT), mice injected intravenously with 1 mg or 1.5 mg glucose per gram of body weight and placed in clean cages. Blood glucose was measured immediately before and at 5, 10, 20, 30, 60 and 120 minutes after the injection of glucose.

Isolation of Pladin by HPLC

Mouse serum was freshly prepared by drawing blood through ophthalmectomy. The sera of plg$^{-/-}$lepr$^{-/-}$ and db/db mice were directly analyzed with Waters Delta 600E/2487/717 HPLC System using a C18 reverse phase column (4.6× 250 mm, 5 µm, Hambon, Zhangjiagang, CN) and eluted with a linear gradient from 20%-40% acetonitrile in 0.1% TFA for 20 minutes at the flow rate of 1 ml/minute (Enriori et al., 2007). Compared with db/db mice, the divergent fractions eluted in plg$^{-/-}$lepr$^{-/-}$ mice were collected for the determination of molecular weight using the Applied Biosystems 4800 Proteomics Analyzer (Applied Biosystems). The MS spectra were acquired in the liner mode at a range of peptide mass from 3,000 to 20,000 Dalton.

Protein Identification by Mass Spectrometry

The samples isolated by HPLC-C18 were further separated by 15% SDS-PAGE. The entire lane of each sample was divided into slices of 1.5 mm width for in-gel tryptic digestion, and then analyzed by tandem mass spectrometry using the Applied Biosystems 4800 Proteomics Analyzer. Both PMF and MS/MS in the reflectron mode analyses were carried out. Proteins were identified by searching against the Swiss-Prot databases using MASCOT (http://www.matrix-science.com/Matrix Science). The searching parameters were used as following, the tolerances for MS and MS/MS-0.3 Da; variable modifications-oxidation (M) and carbamidomethyl (C); enzyme-trypsin.

Intraventricular (i.c.v.) Injection

The animals were pretreated to install an indwelling needle, and allowed a washout period of at least 1 week before the procedure of i.c.v. injection. Without anaesthesia, the testing substance such as nesfatin-1 (25 pmol) or rPladin (25 pmol) was infused into the third ventricle of the brain with a total volume of 5 µL over 5 min. The experiments were carried out at the beginning of the dark cycle (18:00 h) with food and water available freely. Food intake was measured at 3 hours after the i.c.v. injection.

Intravenous (i.v.) or Intraperitoneal (i.p.) Injection

Without anesthesia, mice were placed into a restricting tube. The testing substance such as nesfatin-1 or rPladin was i.v. injected via mice tail vein with a total volume of 150 µL. After that mice were returned to the cages with food and water available freely. In the i.p. injection experiment, mice without anesthesia were injected with the testing substances directly into the peritoneal with a total volume of 200 µL.

Streptozotocin (STZ) Induced Type-1 Diabetic Mice

Male C57BL/6J mice (10 weeks) were intraperitoneally injected with 100 µg/g/day STZ in 100 mmol/L sodium citrate (pH 4.5) on two consecutive days. Blood glucose was measured by tail vein sampling using the glucose oxidase enzymatic test. When the fasting blood glucose reading was over 16 mmol/L after the STZ injection, the mice were considered to be type-1 diabetic. If its blood glucose levels exceeded 30 mmol/L, the diabetic mouse was given 16 ng of porcine insulin (Wangbang, Xuzhou, CN) immediately to prevent the blood glucose being dangerous. rPladin (10 nmol per mouse) was i.v. injected either alone or combined with insulin (2 ng/mouse) subcutaneously to STZ-induced type-1 diabetic mice.

Caloric Restriction db/db mice at 8 weeks of age were divided into following two groups, caloric restricted (CR) and fed with food and water freely (freely fed). While freely fed animals had constant access to food, CR animals were placed onto 30% CR gradually as previously described (Miller et al., 2002), in which they received 90% of the caloric intake of the freely fed counterparts for the 1st week, 80% for the 2nd week, and then 70% for the rest time of the study.

Site-Direct Mutagenesis and Gene Expression of Recombinant Pladin

The cDNA encoding pladin was synthesized according to the amino acid sequence of pladin using the optimized codons for *E. coli*, and then inserted into the His-tagged expression vector, pladin-pET28a. The construct was transformed into the competent *E. coli* strain *Rosetta* cells. The protein expression was induced in 10 liters of bacterial cultures by the addition of 1 mmol/L IPTG. His-tagged rPladin was then purified from soluble lysates of induced bacterial pellets by affinity chromatography of Ni-NTA Superflow (QIAGEN). rPladin was further purified by RP-C18 HPLC after cleavage by enterokinase. The site direct mutants of rPladin were generated with the Mutant BEST Kit (TaKaRa) using the pladin-pET28a plasmid as the template. Recombinant nesfatin-1 was also made accordingly.

Acetylation and Conjugation with Albumin

Acetylated rPladin was prepared using N-acetylimidazole as previously described (Furth and Hope, 1970), and identified with MS spectrum after a preparative RP-C18-HPLC purification. rPladin and acetylated rPladin were also conjugated with bovine serum albumin using SMPT as described (Ding et al., 2003). The conjugates were then purified after the size exclusion chromatography and identified with 10% SDS-PAGE and Gel-filtration HPLC.

Effect of PPAR-γ Antagonist GW9662 and AMPK Inhibitor Compound C on rPladin Reduced Blood Glucose db/db mice of 16 to 18 weeks old were i.v. injected with 0.45 ug/g of GW9662 (Sigma, St. Louis, Mo.), i.p. injected with 20 ug/g rosiglitazone (Sigma, St. Louis, Mo.) or 20 ug/g Compound C (Sigma, St. Louis, Mo.), and then randomly assigned to receive the i.v. injection of 10 nmol rPladin or the same volume of saline as the control. Blood glucose was measured at 3 hours after the injection using the glucose meter (Roche, Indianapolis, Ind.).

Statistical Analysis

Data were presented as means±SEM. as indicated in the figure legends. All data were representative of at least two different experiments. Comparisons between individual data points were made using a two-tailed student's t-test. Differences were considered statistically significant when P was less than 0.05.

EXAMPLE 12

Plasminogen Deficiency in db/db and ob/ob Normalized Blood Glucose and Serum Insulin, and Reduced Body Weight It was observed previously that plasminogen deficient mice were slightly lighter than their wild-type littermates (Hoover-Plow et al., 1999). Promoted by this trivial difference in weight, plasminogen was made deficient in lep$^{-/-}$ (ob/ob) or lepr$^{-/-}$ (db/db) mice to examine whether the weight-reducing effect would remain in these obese animals. Mice without leptin or leptin receptor are obese, diabetic, infertile, hyperphagic and hypoactive (Chua et al., 1996). As reported here, plasminogen deficiency not only significantly reduced obesity in both mice, but also dramatically improved diabetic symptoms in db/db mice. The body weights and food intakes of plg$^{-/-}$lepr$^{-/-}$ and plg$^{-/-}$lep$^{-/-}$ were markedly reduced on chow diet, compared to their obese littermates, while plg$^{+/+}$lepr$^{-/-}$ and db/db weighed same over the age. The high blood glucose (FIG. 7) and insulin of db/db mice were normalized in plg$^{-/-}$lepr$^{-/-}$. In contrast to diabetic plg$^{+/+}$lepr$^{-/-}$, plg$^{-/-}$lepr$^{-/-}$ mice reacted normally to intraperitoneal (i.p.) injected glucose in the i.p. glucose tolerance test (IP-GTT).

EXAMPLE 13

Discovery of Pladin

Figure 8:
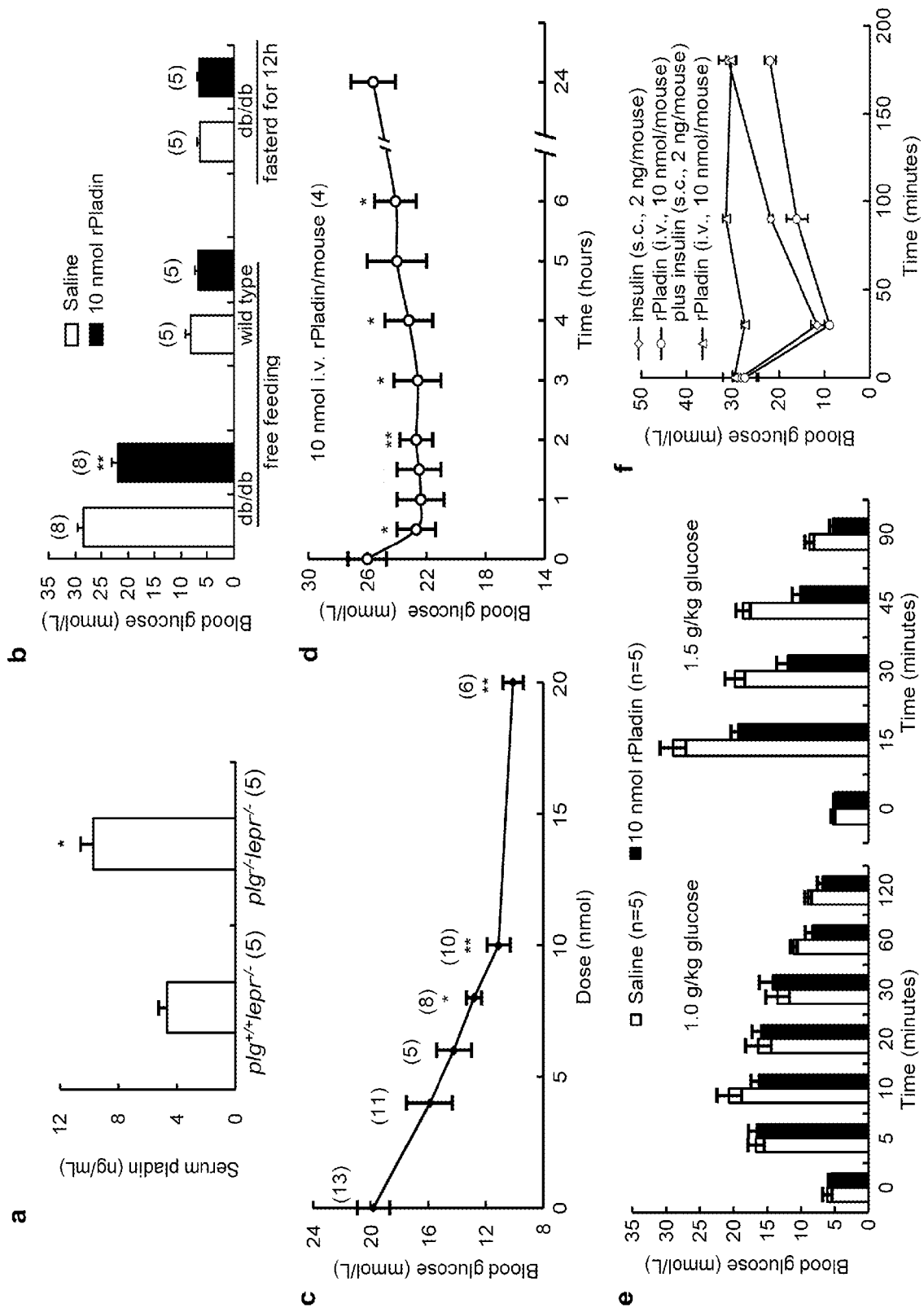
FIG. 8 shows the anti-hyperglycemic effect of rPladin was time-, dose- and insulin dependent: (A) Serum pladin in $plg^{-/-}lepr^{-/-}$ and $plg^{+/+}lepr^{-/-}$ mice. (B) Blood glucose of mice injected with rPladin. (C) The dose-dependent effect of i.v. rPladin. (D) time-dependent effect of i.v. rPladin. (E) The IV-GTT in wild-type mice with i.v. injection of rPladin. (F) The effect of rPladin on Streptozotocin-induced type-1 diabetic C57BL/6J mice, 4 males per group. Data represented the mean±SEM (*, p<0.05, **, p<0.01). Number of mice used showed in parentheses.

Comparing with the serum of db/db, a naturally occurring peptide was found significantly higher in mouse serum of plg$^{-/-}$lepr$^{-/-}$ (FIG. 8A). After isolated by HPLC-C18 (FIG. 9A), the molecular weight of the peptide was determined to be 8,119 Dalton by MALDI-TOF (FIG. 9B) and to contain 69 amino acids by MALDI-TOF/TOF with trypsic peptides (TKVHNTEPVENARIEPPDTGLYYDEY-LKQVIEVLETDPHFREK LQKADIEEIRSGRLSQELD-LVSHKVR) (SEQ ID NO:23) (FIG. 9C-E). It was found as a portion of nucb2 (nucleobindin-2) using BLAST. It is named pladin abbreviated for plasma anti-diabetic nucb2 peptide or plasmin related anti-diabetic nucb2 peptide. Pladin is also found in the plasma of wild-type mouse, rat, rabbit and human. Previously, an 82 amino-acid fragment of nucb2 called nesfatin-1 was postulated based on the putative proteolytic site of prohormone convertases (Oh-I et al., 2006). As a satiety molecule, nesfatin-1 has not been previously reported to have any effects on carbohydrate metabolism, although it contains 69 amino-acid pladin in the molecule (Oh-I et al., 2006; Shimizu et al., 2009). To further investigate these nucb2 peptides, recombinant pladin (rPladin) and nesfatin-1 have been produced in *E. coli* using the pET28a expression vector and purified with HPLC-C18.

EXAMPLE 14

The Anti-Hyperglycemic Effect of rPladin was Time-, Dose- and Insulin Dependent

Freely fed db/db mice had high blood glucose over 25 mmol/L. The intravenous (i.v.) administration of 10 nmol rPladin significantly reduced blood glucose in freely fed db/db, but not in lean wild-type or fasted db/db and mice (FIG. 8B). Furthermore, this anti-hyperglycemic effect was shown to be dose- and time-dependent (FIG. 8CD). During the i.v. glucose tolerance test (IV-GTT) using wild-type mice, 10 nmol rPladin significantly enhanced the uptake of blood sugar with i.v. injection of 1.5 g/kg glucose, but not 1 g/kg (FIG. 8E). The i.v. administration of rPladin did not significantly affect blood insulin in mice including db/db. Based on these observations, it is presumed the anti-hyperglycemic effect of rPladin would be insulin-dependent. Indeed, in Streptozotocin-induced type-1 diabetic mice which had no secretion of insulin, blood glucose was lowered by rPladin only when insulin was also subcutaneously injected (FIG. 8F).

EXAMPLE 15

Figure 10:
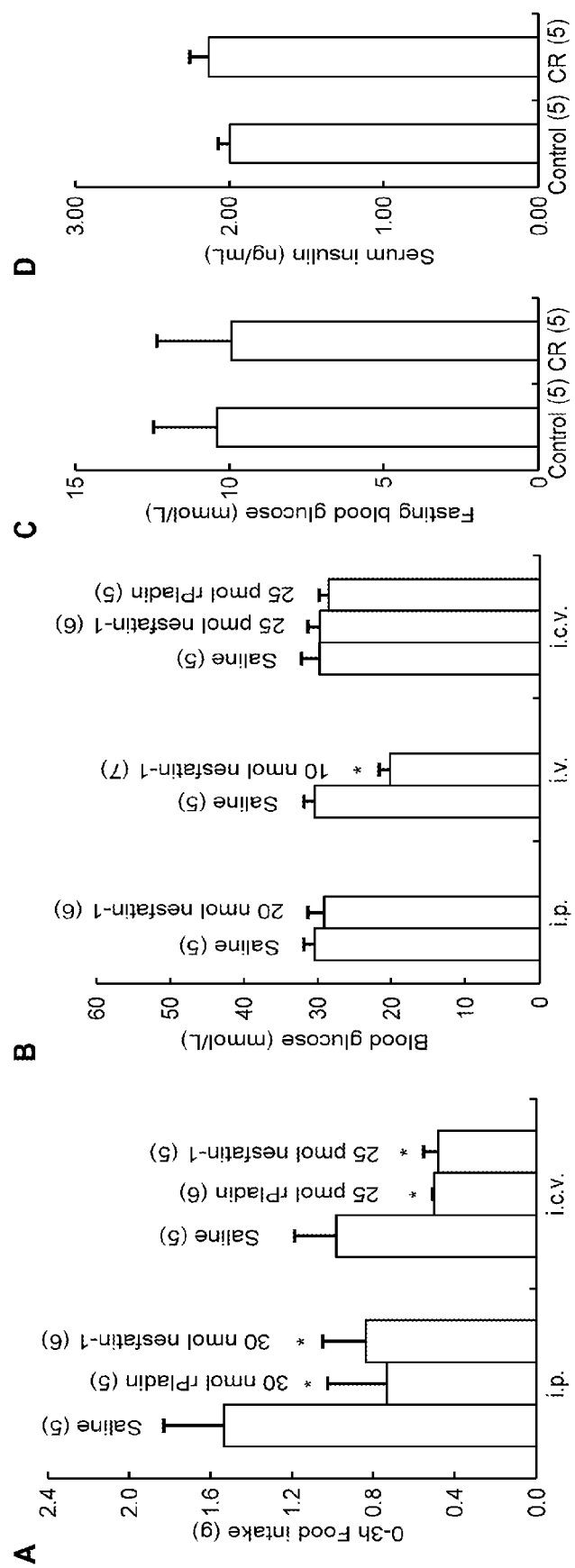
FIG. 10 shows the anorexigenic effect of rPladin was not responsible for the anti-hyperglycemic effect (A) 0-3 h food intake of rat after i.p. and i.c.v. injection of rPladin or nesfatin-1. (B) Blood glucose of db/db mice after i.p., i.v. and i.c.v. injection of nesfatin-1 or rPladin. (C) Fasting blood glucose of caloric restricted db/db mice over 7 weeks. (D) Serum insulin of caloric restricted db/db mice over 7 weeks. Data represented the mean±SEM (*, p<0.05). Number of mice used showed in parentheses.

The Anorexigenic Effect of rPladin was not Responsible for the Anti-Hyperglycemic Activity As potent as nesfatin-1, 30 nmol i.p. or 25 pmol intraventricular (i.c.v.) injection of rPladin per rat significantly inhibited food intake (FIG. 10A). Interestingly, it was found for the first time that i.v. administration of nesfatin-1 (10 nmol) also reduced blood glucose in db/db mice, but not i.p. administration (FIG. 10B). Therefore, it is of interest to further clarify whether the anorexigenic effect of rPladin or nesfatin-1 would be responsible for the anti-hyperglycemic effect.

rPladin or nesfatin-1 i.c.v. injected (25 pmol) to db/db mice significantly inhibited food intake but had no effect on the high levels of blood glucose (FIG. 10B), suggesting that the anti-hyperglycemic effect was peripheral rather than neurological, and unrelated to the anorexigenic effect.

EXAMPLE 16

Caloric Restriction Did not Normalize Blood Glucose in Db/Db Mice

Since plasminogen deficient db/db mice which had higher serum pladin and improved diabetes also significantly reduced food intake (FIG. 8A), it is of interest to verify whether the starvation was responsible for the diabetic improvement. The db/db mice with caloric restriction did not altered the high level of blood glucose and serum insulin (FIG. 10 CD), suggesting that the reduction in food intake was not the key cause of anti-diabetic effect of plasminogen deficiency.

EXAMPLE 17

Pladin was Inactivated by Plasmin

Carefully examining the amino acid sequence of pladin (SEQ ID NO: 23), it has several putative cleavage sites by plasmin (FIG. 11A). Indeed, when rPladin was incubated with plasmin, it was rapidly degraded (FIG. 11B) as well as the anti-hyperglycemic effect was lost (FIG. 11C). Additionally, pladin mutant A4 (Lys28→Ala), A5 (Lys13→Ala) and acetylated rPladin were resistant to plasmin proteolysis (FIG. 11B).

Figure 11:
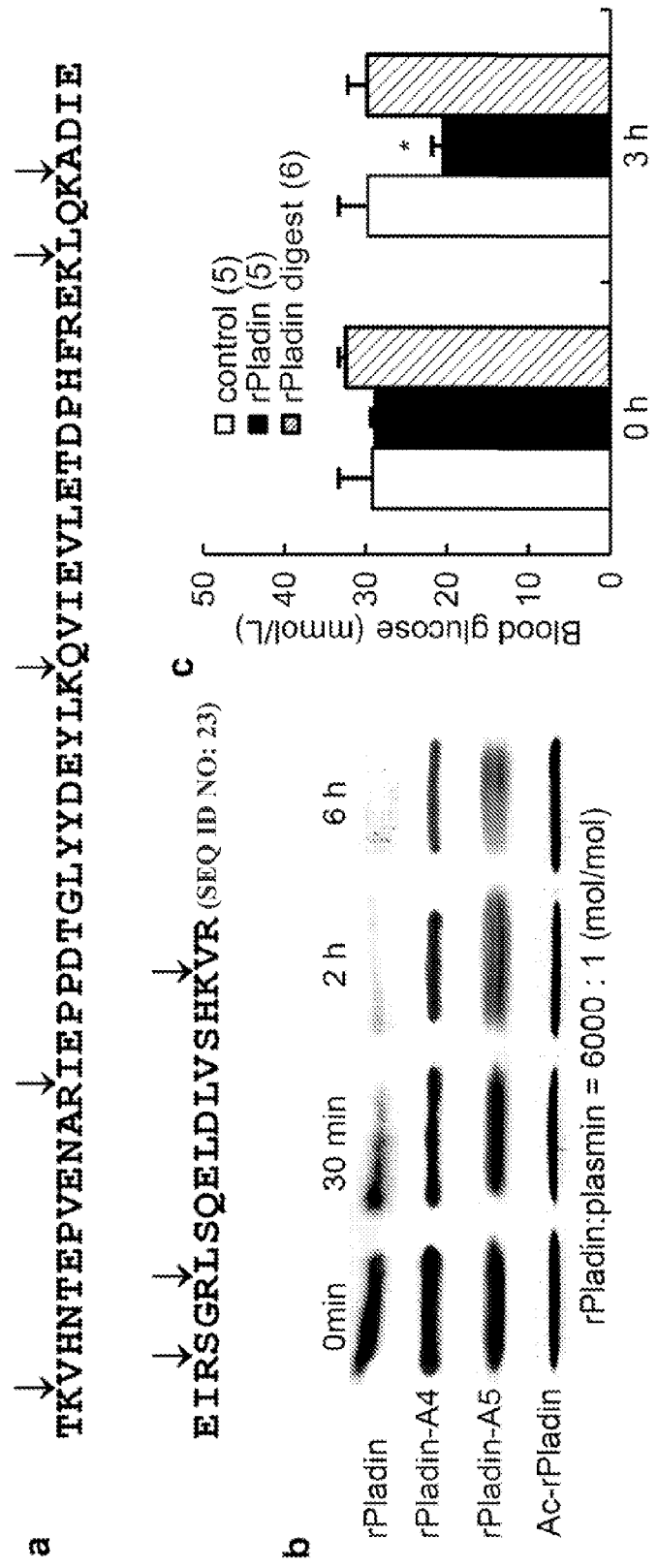
FIG. 11 shows Pladin was inactivated by plasmin in vitro. (A) The amino acid sequence of mouse pladin (SEQ ID NO.: 23). Arrows indicated the putative cleavage sites by plasmin. (B) rPladin and mutants were completely digested by plasmin. (C) Blood glucose of db/db mice after treated with rPladin and plasmin digested rPladin. Data represented the mean±SEM (*, p<0.05). Number of mice used showed in parentheses.

Based on the data in FIG. 11, it is postulated that pladin would be inactivated by plasmin, and at least in-part responsible for the anti-diabetic effect of plasminogen deficiency in db/db mice. Although it is well known that plasmin was generated in circulation (Cushman et al., 1999; Folsom et al., 2001; Sakkinen et al., 1999), it is unknown whether there are any natural substrates of plasmin in circulation other than fibrin.

Figure 12:
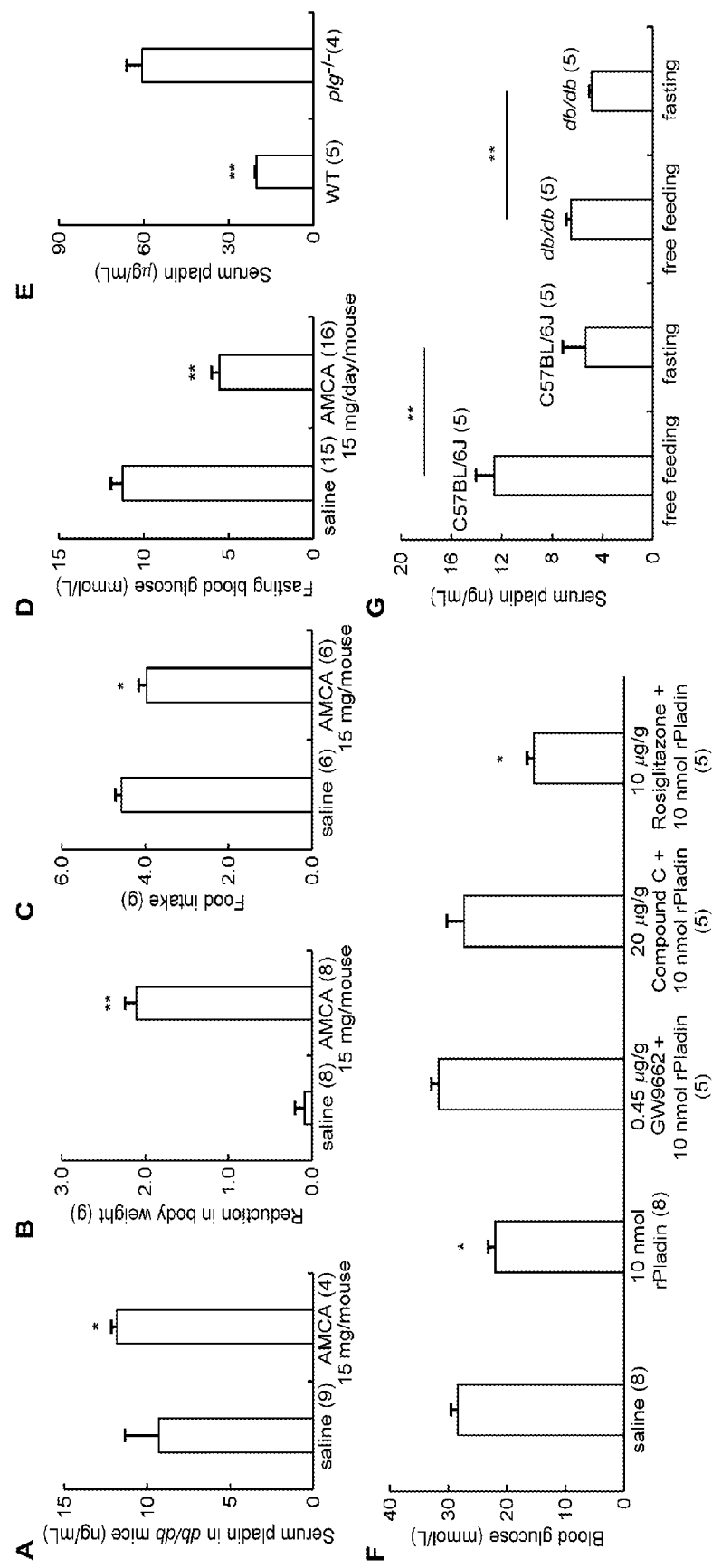
FIG. 12 shows the effect of AMCA, GW9662, Compound C, rosiglitazone, $plg^{-/-}$ and fasting on serum pladin (A) Serum pladin in db/db at 10 minutes after i.v. injection of 15 mg AMCA. The lower pladin in "saline" than "free fed db/db" (FIG. 2A) was due to blood dilution after injection. (B) Reduction in body weight after a 3-day i.v. AMCA (15 mg/day). (C) Food intake at day 3 during a 3-day i.v. AMCA (15 mg/day). (D) Fasting Blood glucose of db/db mice treated with AMCA daily for 10 weeks since 2 weeks old versus the saline controls. (E) Serum pladin in wild-type and $plg^{-/-}$ mice at 10 minutes after i.v. injection of 10 nmol rPladin. (F) Blood glucose of db/db mice at 3 hours after treated with rPladin, GW9662, Compound C or rosiglitazone. (G) Serum pladin in wild-type and db/db mice with freely feeding or fasting. Data represented the mean±SEM (*, p<0.05, **, p<0.01). Number of mice used showed in parentheses.

At first, AMCA (tranexamic acid) was chosen, a potent specific inhibitor for plasmin, to mimic the effect of plasminogen deficiency in db/db mice. Serum pladin was increased in db/db at 10 minutes after i.v. administration of 15 mg AMCA (FIG. 12A), while reductions in food intake and body weight were seen after a once-daily administration for three days (FIG. 12BC). The fasting blood glucose was also reduced significantly when db/db mice received the once-daily administration for 10 weeks since 2 weeks old (FIG. 12D).

Secondly, rPladin i.v. injected cleared much slower in plg$^{-/-}$ than wild-type mice (FIG. 12E), suggesting that plasmin was the possible enzyme to degrade rPladin in vivo.

Figure 13:
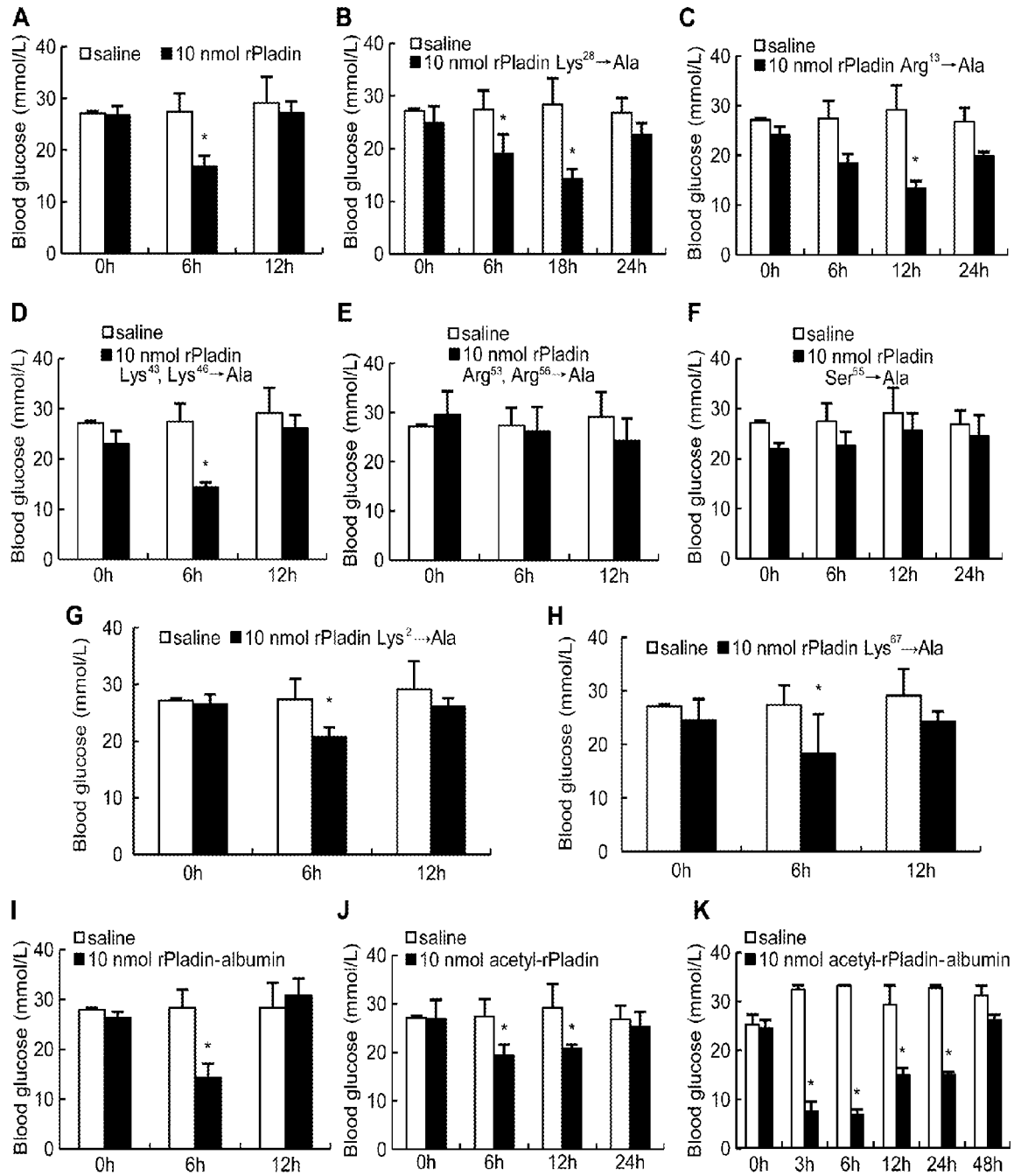
FIG. 13 shows the effect of plasmin-resistant mutations, Ser65, acetylation and albumin conjugation on the anti-hyperglycemic activity of rPladin Blood glucose of db/db mice i.v. injected with (A) rPladin and (B-H) its mutations and (I) rPladin-albumin, (J) acetylated-rPladin, (K) acetylated-rPladin-albumin Five db/db mice were used per group. Data represented the mean±SEM (*, p<0.05).
Figure 14:
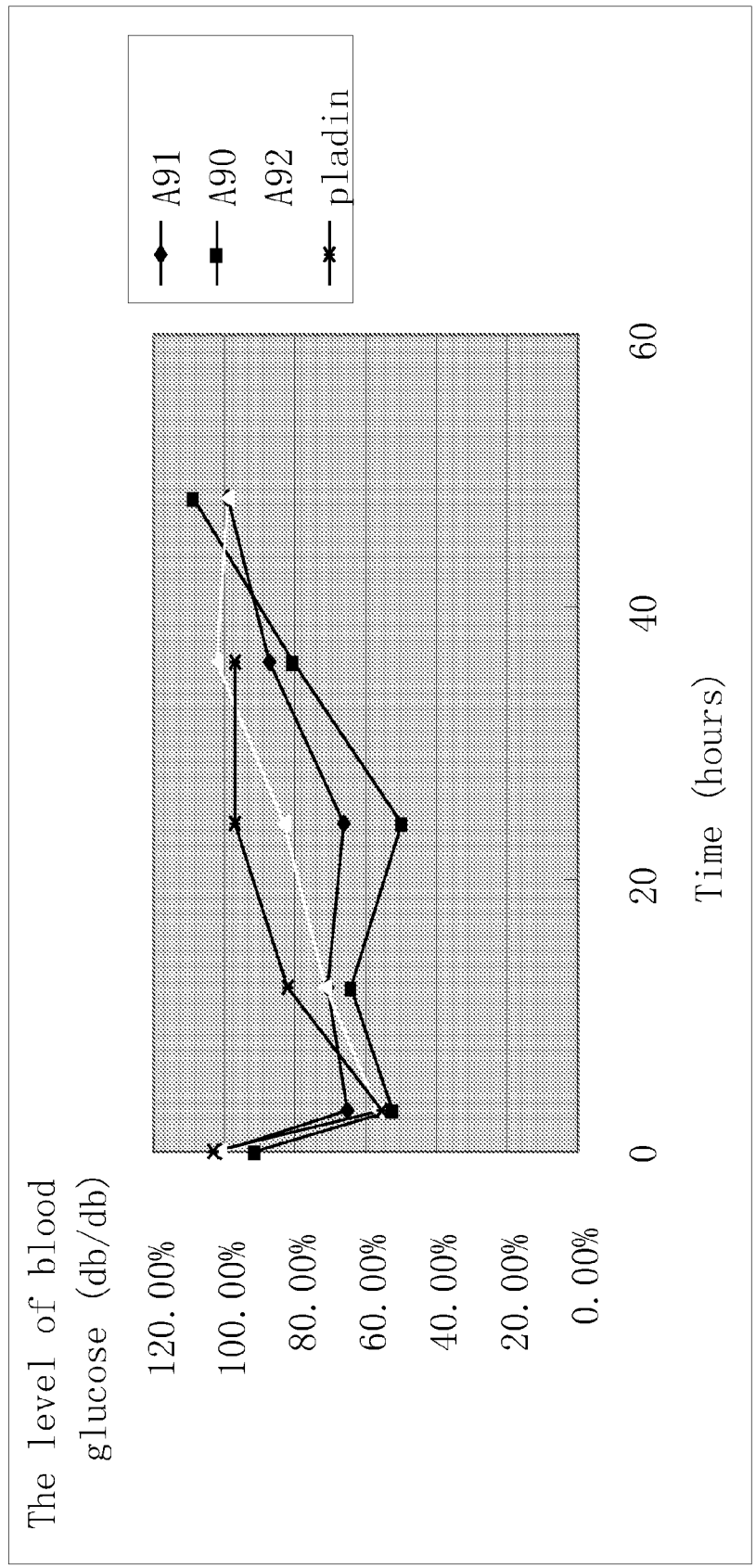
FIG. 14 shows the effect of plasmin-resistant mutations, A90, A91 and A92 on the anti-hyperglycemic activity of rPladin. Blood glucose of db/db mice i.v. injected with rPladin and mutations (10 nmoles). Five db/db mice were used per group.

Thirdly, acetylated rPladin was made in which three Tyr and three Lys residues were modified, as determined with complete lose in absorbance in 280 nm and increase in molecular weight (8,369 versus 8,117 Dalton). The anti-hyperglycemic activity of acetylated rPladin was unchanged but prolonged from 6 to 12 hours after i.v. injection as measured in hyperglycemic db/db mice, in comparison with unmodified rPladin (FIG. 13AJ). It was also found in vitro that acetylated rPladin was resistant to the proteolysis by plasmin (data not shown). The results indicated that the acetylation on these residues did not affect in the activity of pladin, and that plasmin proteolysis at these Lys residues was the important step of the inactivation of pladin.

Finally, a serial of site-directed mutations of Arginine or Lysine to Alanine have been made to protect rPladin from plasmin proteolysis. The Ala mutation at Arg$^{13}$ or Lys$^{28}$ significantly increased the active duration in vivo, from 6 to 12 or 18 hours, respectively (FIG. 13BC). They were also resistant to plasmin proteolysis (FIG. 11B). The Ala mutation at Arg$^{53}$ and Arg$^{56}$ impaired the anti-hyperglycemic activity by five folds, suggesting that the fragment of RSGRLS (53-58) was important for the anti-diabetic effect of pladin (FIG. 13E). The other mutations at Lys$^2$, Lys$^{43}$, Lys$^{46}$ and Lys$^{67}$ did not significantly alter the activity of pladin (FIG. 13DGH).

Taking these data together, it is concluded that pladin was essentially inactivated by plasmin or plasmin-like basic residue specific proteases in vivo. Apparently, the anti-diabetic effect of plasminogen deficiency in db/db mice was due to reduction in the proteolytic inactivation of anti-hyperglycemic pladin.

EXAMPLE 18

Ser$^{65}$ was Critical for Anti-Hyperglycemia

The Ala substitution at Ser65 completely eliminated the anti-hyperglycemic activity of rPladin, implicated that a possible mechanism of phosphorylation at Ser65 could be critical for its interaction with insulin signaling (FIG. 13F).

EXAMPLE 19

The Conjugate of Acetylated Pladin and Albumin Effectively Decreased Blood Glucose without Entering the Brain Since nesfatin-1 was found to affect rats neuropsychologically as evidenced by increasing anxiety and fear-related behaviors (Merali et al., 2008), a long-acting conjugate of acetylated rPladin and albumin has been made which effectively reduced blood glucose without entering the brain (date not shown) and had an active duration more than 36 hours (FIG. 13K). Interestingly, when albumin was conjugated unmodified rPladin, the active duration of the conjugate was same as rPladin (FIG. 13I). This indicated that the conjugation with albumin did not protect rPladin from the proteolytic inactivation.

EXAMPLE 20

The Anti-Hyperglycemic Effect of rPladin In Vivo was Abolished by GW9662 or Compound C but not Rosiglitazone The anti-hyperglycemic effect of rPladin was abolished with pre-injection of the PPAR-γ antagonist, GW9662 and the AMPK inhibitor, Compound C. The pre-treatment of the PPAR-γ agonist, rosiglitazone, did not affect the effect of rPladin (FIG. 12F). It suggested that the anti-hyperglycemic effect of rPladin was definitely associated with the signaling pathways of insulin.

EXAMPLE 21

Mutated rPladin

Mutant A90 of rPladin significantly increased the active duration in vivo for the anti-hyperglycemic effect. The mutant A90 of pladin significantly increased the active duration in vivo, from 6 to >24 hours (FIG. 14).

```
A90
                                                  (SEQ ID NO: 19)
TKVHNTEPVENARIEPPDTGLYYDEYAKAAAAALETDPHFREKLQKADIE

EIRSGRLSQELDLVSHKVR
```

Mutant A91 of rPladin significantly increased the active duration in vivo for the anti-hyperglycemic effect. The mutant A91 of pladin significantly increased the active duration in vivo, from 6 to >24 hours (FIG. 14).

```
A91
                                                  (SEQ ID NO: 20)
TKVHNTEPVENARIEPPDTGLYYDEYSAAAALETDPHFREKLQKADIEEI

RSGRLSQELDLVSHKVR
```

Mutant A92 of rPladin significantly increased the active duration in vivo for the anti-hyperglycemic effect. The mutant A92 of pladin significantly increased the active duration in vivo, from 6 to >12 hours (FIG. 14).

```
A92
                                                  (SEQ ID NO: 21)
TKVHNTEPVENARIEPPDTGLYYDEYAALETDPHFREKLQKADIEEIRSG

RLSQELDLVSHKVR
```

EXAMPLE 22

An Essential Sequence of Pladin for its Anti-Hyperglycemic Effect

A synthetic 20 amino acids peptide of ADIEEIRSGR LSQELDLVSH (SEQ ID NO:22), which was the C-terminal portion of pladin, was anti-hyperglycemic. Its molar anti-hyperglycemic activity was more than 3-fold less than rPladin when it was i.v. injected to db/db mice.

EXAMPLE 23

A NUCB1 Peptide Homologous to the Essential Sequence (20 Residues) of Pladin

A synthetic 20 amino acids peptide of ANAEDIKSGKLSQELDFVSH (SEQ ID NO:24) that is a portion of NUCB1 (nucleobindin-1) was found to be highly homologous to the essential sequence (SEQ ID NO:22) of pladin. It was also anti-hyperglycemic and the molar anti-hyperglycemic activity was similar to that of the essential sequence peptide (SEQ ID NO:22), when it was i.v. injected to db/db mice. Their sequences were aligned as the following.

```
ADIEEIRSGR LSQELDLVSH    (SEQ ID NO: 22)

ANAEDIKSGK LSQELDFVSH    (SEQ ID NO: 24)
```

EXAMPLE 24

Anti-Hyperglycemic Effect of NUCB1

Based on the result of the experiment in Example 23, a 78 amino acids recombinant peptide of NUCB1 (SEQ ID NO:25) which contains the SEQ ID NO:24 has been produced, which was the N-terminal portion of NUCB1. It was also anti-hyperglycemic and the molar anti-hyperglycemic activity was at least 2-fold higher than that of rPladin or nesfatin-1 after it was i.v. injected to db/db mice within 3 hours. However, its active duration was at least 2-fold less than that of rPladin or nesfatin-1 in vivo. SEQ ID NO:25 has 68% sequence homology with pladin.

```
                                                  (SEQ ID NO: 25)
VPVDRAAPPQ EDSQATETPD TGLYYHRYLQ EVINVLETDG

HFREKLQAAN AEDIKSGKLS QELDFVSHNV RTKLDELK
```

Sequence alignment between pladin (SEQ ID NO:23) and a NUCB1 peptide (SEQ ID NO:25):

```
                                                  SEQ ID NO: 23
--TKVHNTEPVENARIEPPDTGLYYDEYLKQVIEVLETDPHFRE

SEQ ID NO: 25
VPVDRAAPPQEDSQATETPDTGLYYHRYLQEVINVLETDGHFRE

SEQ ID NO: 23
KLQKADIEEIRSGRLSQELDLVSHKVR

SEQ ID NO: 25
KLQAANAEDIKSGKLSQELDFVSHNVRTKLDELK
```

REFERENCES

1. Krystosek, A. & Seeds, N. W., Plasminogen activator release at the neuronal growth cone. *Science* 213 (4515), 1532-1534 (1981).
2. Moonen, G., Grau-Wagemans, M. P., & Selak, I., Plasminogen activator-plasmin system and neuronal migration. *Nature* 298 (5876), 753-755 (1982).
3. Tsirka, S. E., Rogove, A. D., Bugge, T. H., Degen, J. L., & Strickland, S., An extracellular proteolytic cascade promotes neuronal degeneration in the mouse hippocampus. *J Neurosci* 17 (2), 543-552 (1997).
4. Wang, N., Zhang, L., Miles, L., & Hoover-Plow, J., Plasminogen regulates pro-opiomelanocortin processing. *J Thromb Haemost* 2 (5), 785-796 (2004).
5. Hoover-Plow, J., Wang, N., & Ploplis, V., Growth and behavioral development in plasminogen gene-targeted mice. *Growth Dev Aging* 63 (1-2), 13-32 (1999).
6. Chua, S. C. et al., Phenotypes of mouse diabetes and rat fatty due to mutations in the OB (leptin) receptor. *Science* 271 (5251), 994-996 (1996).
7. Oh-I, S. et al., Identification of nesfatin-1 as a satiety molecule in the hypothalamus. *Nature* 443 (7112), 709-712 (2006).
8. Shimizu, H. et al., Peripheral administration of nesfatin-1 reduces food intake in mice: the leptin-independent mechanism. *Endocrinology* 150 (2), 662-671 (2009).
9. Price, T. O., Samson, W. K., Niehoff, M. L., & Banks, W. A., Permeability of the blood-brain barrier to a novel satiety molecule nesfatin-1. *Peptides* 28 (12), 2372-2381 (2007).

10. Pang, P. T. et al., Cleavage of proBDNF by tPA/plasmin is essential for long-term hippocampal plasticity. *Science* 306 (5695), 487-491 (2004).
11. Zhang, L., Gong, Y., Grella, D. K., Castellino, F. J., & Miles, L. A., Endogenous plasmin converts Glu-plasminogen to Lys-plasminogen on the monocytoid cell surface. *J Thromb Haemost* 1 (6), 1264-1270 (2003).
12. Pan, W., Hsuchou, H., & Kastin, A. J., Nesfatin-1 crosses the blood-brain barrier without saturation. *Peptides* 28 (11), 2223-2228 (2007).
13. Merali, Z., Cayer, C., Kent, P., & Anisman, H., Nesfatin-1 increases anxiety- and fear-related behaviors in the rat. *Psychopharmacology (Berl)* 201 (1), 115-123 (2008).
14. Selvarajan, S., Lund, L. R., Takeuchi, T., Craik, C. S., & Werb, Z., A plasma kallikrein-dependent plasminogen cascade required for adipocyte differentiation. *Nat Cell Biol* 3 (3), 267-275 (2001).
15. Zheng, F. et al., Development of albuminuria and glomerular lesions in normoglycemic B6 recipients of db/db mice bone marrow: the role of mesangial cell progenitors. *Diabetes* 53 (9), 2420-2427 (2004).
16. Hastings, G. A. et al., Neuroserpin, a brain-associated inhibitor of tissue plasminogen activator is localized primarily in neurons Implications for the regulation of motor learning and neuronal survival. *J Biol Chem* 272 (52), 33062-33067 (1997).
17. Cota, D. et al., Hypothalamic mTOR signaling regulates food intake. *Science* 312 (5775), 927-930 (2006).
18. Cushman, M., Lemaitre, R. N., Kuller, L. H., Psaty, B. M., Macy, E. M., Sharrett, A. R., and Tracy, R. P. (1999). Fibrinolytic activation markers predict myocardial infarction in the elderly. The Cardiovascular Health Study. Arterioscler Thromb Vasc Biol 19, 493-498.
19. Ding, B. S., Zhou, Y. J., Chen, X. Y., Zhang, J., Zhang, P. X., Sun, Z. Y., Tan, X. Y., and Liu, J. N. (2003). Lung endothelium targeting for pulmonary embolism thrombolysis. Circulation 108, 2892-2898.
20. Enriori, P. J., Evans, A. E., Sinnayah, P., Jobst, E. E., Tonelli-Lemos, L., Billes, S. K., Glavas, M. M., Grayson, B. E., Perello, M., Nillni, E. A., Grove, K. L., and Cowley, M. A. (2007). Diet-induced obesity causes severe but reversible leptin resistance in arcuate melanocortin neurons. Cell Metab 5, 181-194.
21. Folsom, A. R., Aleksic, N., Park, E., Salomaa, V., Juneja, H., and Wu, K. K. (2001). Prospective study of fibrinolytic factors and incident coronary heart disease: the Atherosclerosis Risk in Communities (ARIC) Study. Arterioscler Thromb Vasc Biol 21, 611-617.
22. Furth, A. J., and Hope, D. B. (1970). Studies on the chemical modification of the tyrosine residue in bovine neurophysin-II. Biochem J 116, 545-553.
23. Gonzalez, R., Tiwari, A., and Unniappan, S. (2009). Pancreatic beta cells colocalize insulin and pronesfatin immunoreactivity in rodents. Biochem Biophys Res Commun 381, 643-648.
24. Miller, R. A., Chang, Y., Galecki, A. T., Al-Regaiey, K., Kopchick, J. J., and Bartke, A. (2002). Gene expression patterns in calorically restricted mice: partial overlap with long-lived mutant mice. Mol Endocrinol 16, 2657-2666.
25. Moller, D. E. (2001). New drug targets for type 2 diabetes and the metabolic syndrome. Nature 414, 821-827.
26. Pan, W., Hsuchou, H., and Kastin, A. J. (2007). Nesfatin-1 crosses the blood-brain bather without saturation. Peptides 28, 2223-2228.
27. Sakkinen, P. A., Cushman, M., Psaty, B. M., Rodriguez, B., Boineau, R., Kuller, L. H., and Tracy, R. P. (1999). Relationship of plasmin generation to cardiovascular disease risk factors in elderly men and women. Arterioscler Thromb Vasc Biol 19, 499-504.
28. Stengel, A., Goebel, M., Yakubov, I., Wang, L., Witcher, D., Coskun, T., Tache, Y., Sachs, G., and Lambrecht, N. W. (2009). Identification and characterization of nesfatin-1 immunoreactivity in endocrine cell types of the rat gastric oxyntic mucosa. Endocrinology 150, 232-238.
29. Wang, N., Zhang, L., Miles, L., and Hoover-Plow, J. (2004). Plasminogen regulates pro-opiomelanocortin processing. Journal of thrombosis and haemostasis: JTH 2, 785-796.

What is claimed is:

1. A method of lowering blood glucose in a subject having diabetes comprising the step of administering to said subject a composition comprising an effective amount of an insulin helper pladin (plasma anti-diabetic nucb2 peptide) consisting of the amino acid sequence of SEQ ID NO: 23.

2. The method of claim 1, wherein the composition is administered intravenously, subcutaneously, or orally.

3. The method of claim 1, wherein the pladin has a mutation at $Arg^{13}$ or $Lys^{28}$.

4. The method of claim 1, wherein the pladin is conjugated with one or more molecules to increase its molecular weight.

5. The method of claim 4, wherein the conjugated molecule reduces blood glucose without penetration of blood-brain barrier.

6. The method of claim 1, wherein when the subject is having type 2 diabetes, the method further comprises the step of administering insulin to the subject.

7. A recombinant pladin (plasma anti-diabetic nucb2 peptide) consisting of the amino acid sequence of SEQ ID NO: 23.

8. A recombinant pladin (plasma anti-diabetic nucb2 peptide) consisting of the amino acid sequence of SEQ ID NO: 23, wherein the pladin has a mutation at $Arg^{13}$ or $Lys^{28}$.

9. A composition comprising the pladin of claim 1.

* * * * *